United States Patent
Bracht

(10) Patent No.: US 11,212,990 B2
(45) Date of Patent: Jan. 4, 2022

(54) MAIZE INBRED SG350

(71) Applicant: AgriHorizon, Inc., Fremont, NE (US)

(72) Inventor: Dennis Bracht, Arlington, NE (US)

(73) Assignee: AGRIHORIZON, INC., Fremont, NE (US)

( * ) Notice: Subject to any disclaimer, the term of this patent is extended or adjusted under 35 U.S.C. 154(b) by 0 days.

(21) Appl. No.: 16/829,628

(22) Filed: Mar. 25, 2020

(65) Prior Publication Data

US 2020/0305377 A1  Oct. 1, 2020

Related U.S. Application Data

(60) Provisional application No. 62/826,021, filed on Mar. 29, 2019.

(51) Int. Cl.
*A01H 5/10* (2018.01)
*A01H 6/46* (2018.01)

(52) U.S. Cl.
CPC ............. *A01H 6/4684* (2018.05); *A01H 5/10* (2013.01)

(58) Field of Classification Search
CPC combination set(s) only.
See application file for complete search history.

(56) References Cited

U.S. PATENT DOCUMENTS 10,334,804 B1 * 7/2019 Holland ................. A01H 4/008

* cited by examiner

*Primary Examiner* — Brent T Page
(74) *Attorney, Agent, or Firm* — Womble Bond Dickinson (US) LLP

(57) ABSTRACT

The present invention provides the inbred maize variety designated SG350 and relates to all plant parts and tissue cultures of variety SG350. The invention further encompasses methods for producing derivations of variety SG350 such as gene-edited plants, transgenically-modified plants or trait integrated plants, and to all plant parts and tissues derived from such methods. The invention further relates to maize seeds and plants produced by crossing inbred SG350 with itself, or with another maize plant. The invention further relates to the inbred and hybrid genetic and/or genomic complements of variety SG350 plants, seeds, and tissues.

20 Claims, No Drawings

MAIZE INBRED SG350

FIELD OF THE INVENTION

The invention relates generally to the field of maize (*Zea mays* L.) breeding. Specifically, the invention relates to the maize inbred variety SG350, as well as derivatives, hybrids, and tissue cultures thereof.

BACKGROUND OF THE INVENTION

The goal of field crop breeding is to combine various desirable traits in a single variety. Such desirable traits include greater harvestable yield, better stalks, better roots, resistance to insecticides, herbicides, pests, and disease, tolerance to heat and drought, reduced time to crop maturity, better agronomic quality, higher nutritional value, and uniformity in germination times, stand establishment, growth rate, maturity, and fruit size.

Corn is a monecious plant having separate male and female flowers on the same plant. Male flowers that produce the pollen are located in the tassel at the top of the plant, while female flowers that produce ovules and silks are located in the ear that develops from the axil of a leaf and which generally is located near the middle of the stalk.

Corn breeding techniques take advantage of two methods of pollination; self-pollination and cross-pollination. A plant self-pollinates if pollen from the tassel (male flower) of a plant falls upon the silks (female flower) of the same plant. A plant cross pollinates if pollen from one corn plant falls upon the silks of a different corn plant. Natural pollination occurs in a corn field when wind blows pollen from the tassels to the emerged silks that protrude from the tops of the ear shoots. This natural or open pollination in a field results in the corn being mostly cross-pollinated as the wind is essential for good field pollinations. When breeding corn, the tassels and the silks are covered by the breeder with bags to prevent uncontrolled self or cross pollinations. Pollinations for breeding purposes are always controlled. The initial pollination is made to allow specific genetics of one plant to be manually combined with the specific genetics of another plant through techniques in the art. Later generational pollinations are also controlled either manually or by spatial separation to preserve or fix the genetics initially made. Thus, the variety SG350 provided here is a purposeful invention created by careful and skillful planning and execution of the breeding operations.

Corn plants that have been self-pollinated and selected for type over many generations become homozygous at almost all gene loci and produce a uniform population of true breeding progeny, a homozygous inbred plant. A cross between two genetically different such homozygous inbred plants produces a uniform population of hybrid plants that are heterozygous for many gene loci. Conversely, a cross of two (non-inbred) plants each heterozygous at a number of loci produces a population of hybrid plants that differ genetically and are not uniform. The resulting non-uniformity makes performance unpredictable.

Another method for developing uniform homozygous corn inbreds is through use of the Doubled Haploid methods. One such DH method comprises controlled cross pollination of the desired genetics with an inducer line, which following selection serves to develop a haploid population of the desired genetics. Following the doubling procedure to develop diploid plants from the haploid plants, a population of uniform homozygous inbred seed results.

The development of uniform corn plant hybrids requires the development of homozygous inbred plants, the crossing of these inbred plants, and the evaluation of the crosses. Pedigree breeding and recurrent selection are examples of breeding methods used to develop inbred plants from breeding populations. Those breeding methods combine the genetic backgrounds from two or more inbred plants or various other broad-based sources into breeding pools from which new inbred plants are developed by selfing or DH methods, followed by selection of desired phenotypes. The new inbreds are crossed with other inbred plants and the hybrids from these crosses are evaluated to determine which of those have commercial potential.

SUMMARY OF THE INVENTION

According to the invention, a novel maize (*Zea mays* L.) inbred variety designated SG350 is provided and processes for making SG350. This invention relates to seed of maize variety SG350, to the plants of maize variety SG350, to all plant parts of maize variety SG350, and to processes for making a maize plant that comprises crossing maize variety SG350 with another maize plant. This invention also relates to processes for making a maize plant containing in its genetic material one or more traits or alleles or genes introgressed into SG350 through backcross conversion and/or transformation and/or gene-editing, and to the maize seed, plant and plant parts produced thereby. This invention further relates to a hybrid maize seed, plant or plant part produced by crossing the variety SG350 or a locus conversion of SG350 with another maize variety, or other derivations of, or from, variety SG350.

Definitions

Certain definitions used in the specification are provided below. Also, in the examples that follow, a number of terms are used herein. In order to provide a clear and consistent understanding of the specification and claims, including the scope to the given terms, the following definitions are provided. These designators will follow the descriptors to denote how the values are to be interpreted. Below also are the descriptors used in the data tables included herein.

ABIOTIC STRESS TOLERANCE: Resistance to non-biological sources of stress conferred by traits such as nitrogen utilization efficiency, altered nitrogen responsiveness, drought resistance, cold or heat resistance, and salt resistance.

ALLELE: Any of one or more alternative forms of a genetic sequence for a particular gene. In a diploid cell or organism, the two alleles of a given sequence typically occupy corresponding loci on a pair of homologous chromosomes.

ALTER: The utilization of up-regulation, down-regulation, or gene silencing of an allele or gene.

ANC=ANTHER COLOR: Rated on a 1 to 9 Scale where 1 is green, 2 is yellow, 3 is pink, 5 is red, 7 is dark red, and 9 is purple.

ANTHESIS: The time of a flower's opening; usually with respect to anther appearance due to glume opening.

ANTHRACNOSE STALK ROT (*Colletotrichum graminicola*): A 1 to 9 visual rating indicating the resistance to Anthracnose Stalk Rot. A higher score indicates a higher resistance. Data are collected only when sufficient selection pressure exists in the experiment measured.

ANTIOXIDANT: A chemical compound or substance that inhibits oxidation, including but not limited to tocopherol or tocotrienols.

BACKCROSSING: Process in which a breeder crosses a hybrid progeny variety back to one of the parental genotypes one or more times. The parent used for backcrossing is referred to as the recurrent parent.

BACKCROSS PROGENY: Progeny plants produced by crossing SG350 with plants of another maize line that comprise a desired trait or locus, selecting F1 progeny plants that comprise the desired trait or locus, and crossing the selected F1 progeny plants with the SG350 plants one or more times to produce backcross progeny plants that comprise said trait or locus.

BNP=BARREN PLANTS: The percent of plants per plot that were barren (lack ears).

BRC=BRACE ROOT COLOR: A measure of the anthocyanin color intensity of the brace roots rated on a 1 to 4 scale where 1 is absent, 2 is faint, 3 is moderate, and 4 is dark. Observed when well developed and fresh brace roots are present on 50% of plants.

BREEDING: The genetic manipulation of living organisms.

BREEDING CROSS: An initial cross to introduce new genetic material into a plant for the development of a new variety. For example, one could cross plant A with plant B, wherein plant B would be genetically different from plant A. After the breeding cross, the resulting F1 plants could then be selfed or ribbed for one, two, three or more times (F1, F2, F3, etc.) until a new inbred variety is developed; or the resulting F1 or F2 breeding cross could be subjected to one of several Doubled Haploid methods to develop a new uniform inbred variety.

BREEDING VALUE: A relative value determined by evaluating the progeny of the parent. For corn the progeny is often the F1 generation and the parent is often an inbred variety.

BSNP=BRITTLE SNAP PERCENTAGE: Also called Green Snap; the percentage of plants showing pre-anthesis stalk breakage below the top ear node. Usually the result of a high damaging wind event.

CARBOHYDRATE: Organic compounds comprising carbon, oxygen and hydrogen, including sugars, starches and cellulose.

CBC=COB COLOR: A measure of the coloration of the cob rated on a 1 to 4 scale where 1 is white, 2 is pink, 3 is red, 4 is dark red or other.

CBD=COB DIAMETER: Measured in mm as the width of the shelled cob at the mid-point; between the tip and base of the cob.

CELL: A cell as used herein includes a plant cell, whether isolated in tissue culture or incorporated in a plant or plant part.

COMMON SMUT: This is the percentage of plants infected with Common Smut. Data are collected only when sufficient selection pressure exists in the experiment measured.

COMMON RUST (*Puccinia sorghi*): A 1 to 9 visual rating indicating the resistance to Common Rust. A higher score indicates a higher resistance. Data are collected only when sufficient selection pressure exists in the experiment measured.

CROSSING: The combination of genetic material by traditional methods such as a breeding cross or backcross, but also including protoplast fusion and other molecular biology methods of combining genetic material from two sources.

CROSS POLLINATION: Fertilization by the union of two gametes from different plants.

D and D1-Dn: represents various generations of doubled haploids.

DEP=DROPPED EARS: A measure of the number of dropped ears per plot and represents the percentage of plants with dropped ears prior to harvest. Data are collected only when sufficient selection pressure exists in the experiment measured.

DH=DOUBLED HAPLOID: A homozygous and genetically stable diploid plant variety developed through the use of one of several Doubled Haploid methods as opposed to multiple generations of selfing to attain near homozygosity. A plant variety developed by going through haploidization and then genome doubling.

*DIPLODIA* EAR MOLD SCORES (*Diplodiamaydis* and *Diplodia macrospora*): A 1 to 9 visual rating indicating the resistance to *Diplodia* Ear Mold. A higher score indicates a higher resistance. Data are collected only when sufficient selection pressure exists in the experiment measured.

DIPLOID PLANT PART: Refers to a plant part or cell that has the same diploid genotype as SG350.

DIPROTEDIPLODLA STALK ROT SCORE: Score of stalk rot severity due to *Diplodia* (*Diplodia maydis*). Expressed as a 1 to 9 score with 9 being highly resistant. Data are collected only when sufficient selection pressure exists in the experiment measured.

DROUGHT TOLERANCE: This represents a 1 to 9 rating for drought tolerance and is based on data obtained under stress conditions. A high score indicates good drought tolerance and a low score indicates poor drought tolerance. Data are collected only when sufficient selection pressure exists in the experiment measured.

EARLY STAND COUNT: This is a measure of the stand establishment in the spring and represents the number of plants that emerge on a per plot basis for the inbred or hybrid.

EAR LEAF: The leaf attached to the stalk at the node where the highest significant ear develops.

EHT=EAR HEIGHT: A measure in cm from the ground to the highest developed ear node.

ELL=EAR LEAF LENGTH: A measure in cm of the length of the ear leaf blade.

EAR LEAF NODE: The node on the stalk from which the highest significant ear develops and from which the ear leaf develops.

ELW=EAR LEAF WIDTH: A measure in cm of the width of the ear leaf blade at the mid-point between the tip and the leaf collar.

ENDC=ENDOSPERM COLOR: A measure of the coloration of the kernel endosperm rated on a 1 to 3 scale where 1 is white, 2 is yellow, and 3 is other.

ENDT=ENDOSPERM TYPE OR TYPE OF GRAIN: Observed in the middle of the uppermost ear at harvest. Rated as a 1 to 10 classification where 1 is sweet (su1), 2 is extra sweet (sh2), 3 is normal starch, 4 is high amylose starch, 5 is waxy starch, 6 is high protein, 7 is high lysine, 8 is super sweet (se), 9 is high oil, and 10 is other.

ERD=EAR DIAMETER: Measured in mm as the width of the ear at the mid-point; between the tip and base of the ear.

ERKR=EAR KERNEL ROWS: The average number of kernels per row on the ear.

ERL=EAR LENGTH: Measured in cm the length from the ear tip to base.

ERP=EAR POSITION: Measured at the dry husk stage on a 1 to 3 scale where 1 is upright, 2 is horizontal, and 3 is pendent.

ERPSTK=EARS PER STALK: The average number of ears on each plant or stalk. Secondary ears are defined as those with developed or developing kernels.

ERRD=EAR ROW DIRECTION: The kernel row alignment on a 1 to 3 scale where 1 is straight, 2 is slightly curved, and 3 is spiral.

ERRI=EAR ROWS IDENTIFIABLE: The observation of the kernel row identification where 1 is indistinct and 2 is distinct.

ERRN=NUMBER OF ROWS OF KERNELS ON THE EAR: The number of rows of kernels on an ear; usually 12-18 rows.

ERT=EAR SHAPE (TAPER): The taper of the ear from base to tip on a 1 to 3 scale where 1 is slight (cylindrical), 2 is average, and 3 is extreme (conical).

ERWT=EAR WEIGHT: The weight of the intact kernels plus cob measured in grams.

ESSENTIAL AMINO ACIDS: Amino acids that cannot be synthesized by an organism and therefore must be supplied in the diet.

EXPRESSING: With respect to a gene or allele that is partially or wholly causative of a particular measurable or visual phenotype. A situation or environmental setting whereby a phenotype is manifest on the plant.

EXTRACTABLE STARCH: Near-infrared transmission spectroscopy, NIT, prediction of extractable starch.

EYE SPOT (*Kabatiella zeae* or *Aureobasidium zeae*): A 1 to 9 visual rating indicating the resistance to Eye Spot. A higher score indicates a higher resistance. Data are collected only when sufficient selection pressure exists in the experiment measured.

F1 PROGENY: The progeny plants produced by crossing a plant of one maize variety with a plant of another maize variety.

FATTY ACID: A carboxylic acid (or organic acid), often with a long aliphatic tail (hydrocarbon chain), either saturated or unsaturated.

*FUSARIUM* EAR ROT SCORE (*Fusarium moniliforme* or *Fusarium subglutinans*): A 1 to 9 visual rating indicating the resistance to *Fusarium* Ear Rot. A higher score indicates a higher resistance. Data are collected only when sufficient selection pressure exists in the experiment measured.

GDU=GROWING DEGREE UNITS: Using the Barger Heat Unit Theory, which assumes that maize growth occurs in the temperature range 50 degrees F. to 86 degrees F. and that temperatures outside this range slow down growth; the maximum daily heat unit accumulation is 36 and the minimum daily heat unit accumulation is 0. The seasonal accumulation of GDU is a major factor in determining maturity zones. Growing degree units are calculated by the Barger Method, where the heat units for a 24-hour period are:

$$GDU=[(\text{Maximum temperature}+\text{Minimum temperature})/2]-50$$

The highest maximum temperature used is 86 degrees F. and the lowest minimum temperature used is 50 degrees F. For each inbred or hybrid, it takes a certain number of GDUs to reach various stages of plant development.

GENERAL EAR MOLD: Visual rating (1 to 9 score) where a 1 is very susceptible and a 9 is very resistant. This is based on overall rating for ear mold of mature ears without determining the specific mold organism and may not be predictive for a specific ear mold. Data are collected only when sufficient selection pressure exists in the experiment measured.

GENETIC DERIVATIVE or VARIANT: A variety that has undergone minor genetic modifications as to retain the overall genetics of the variety. Minor genetic modifications would include but are not limited to a mutation, a locus conversion, a somoclonal variant, or a variant derived through gene editing methods.

GENE EDITING or GENOME EDITING: Technologies used to precisely change the DNA in a plant or other organism. Possible changes might include but are not limited to mutate an allele, increase or decrease the expression of an allele, or add or remove an allele. Generally, these genomic changes are enabled through the use of various nucleases, and the genes or alleles changed are of the plant species being altered as opposed to adding alleles or genes from a different species. These technologies also allow the simultaneous gene-editing of multiple alleles during the same procedure. In general, gene-editing is thought to be another breeding tool for adding genetic diversity; an important basis for heterosis and higher plant performance.

GENE SILENCING: The interruption or suppression of the expression of a gene or allele at the level of transcription or translation.

GENOMIC SELECTION: A family of breeding processes and tools whereby the components of the genetic gain equation are manipulated to increase genetic gain. At the heart of each process is the development of a training set of genetics whereby both genotype and phenotype are determined experimentally, followed by development of a predictive equation that can be used to predict phenotype of unknown varieties by only having determined their genotype. Varieties with the best predictive breeding values are then recycled into the breeding population for rapid population improvement and/or advanced for commercial hybrid production. The importance of specific traits in these equations is pre-determined by the breeding objectives for the specific breeding program.

GENOTYPE: Refers to the genetic make-up and/or DNA profile of a cell or organism.

*GIBBERELLA* EAR ROT (PINK MOLD) (*Gibberella zeae*): A 1 to 9 visual rating indicating the resistance to *Gibberella* Ear Rot. A higher score indicates a higher resistance. Data are collected only when sufficient selection pressure exists in the experiment measured.

*GIBBERELLA* STALK ROT SCORE: Score of stalk rot severity due to *Gibberella* (*Gibberella zeae*). Expressed as a 1 to 9 score with 9 being highly resistant. Data are collected only when sufficient selection pressure exists in the experiment measured.

GMC=GLUME COLOR: Rated on a 1 to 9 scale where 1 is green, 2 is yellow, 3 is pink, 5 is red, 7 is dark red, and 9 is purple.

GMR=GLUME RING or GLUME BAND: Dark colored ring immediately below the glume if present. Recorded as present or absent.

GOSS'S WILT (*Corynebacterium nebraskense*): A 1 to 9 visual rating indicating the resistance to Goss's Wilt. A higher score indicates a higher resistance. Data are collected only when sufficient selection pressure exists in the experiment measured.

GRAIN OIL: Absolute value of oil content of the kernel as predicted by near-infrared transmittance and expressed as a percent of dry matter.

GRAIN PROTEIN: Absolute value of protein content of the kernel as predicted by near-infrared transmittance and expressed as a percent of dry matter.

GRAIN STARCH: Absolute value of starch content of the kernel as predicted by near-infrared transmittance and expressed as a percent of dry matter.

GRAY LEAF SPOT (Cercospora zeae-maydis): A 1 to 9 visual rating indicating the resistance to Gray Leaf Spot. A higher score indicates a higher resistance. Data are collected only when sufficient selection pressure exists in the experiment measured.

GSP=GREEN SNAP or BRITTLE SNAP: Refers to breakage of the corn stalk completely (or mostly) prior to Bilking due to high winds.

H and H1: Refers to the haploid generation of a Doubled Haploid process.

HAPLOID PLANT PART: Refers to a plant part or cell that has a haploid genotype.

HARD=NUMBER OF DAYS FROM SILKING TO HARVEST: The number of days required for an inbred variety or hybrid to develop from 50 percent of the plants silking to harvest at 25% kernel moisture.

HARGDU=GDU FROM SILKING TO HARVEST: The number of growing degree units (GDUs) or heat units required for an inbred variety or hybrid to develop from 50 percent of the plants silking to harvest at 25% kernel moisture. Growing degree units are calculated by the Barger Method as given in the GDU definition.

HKCD=HUSK DRY COLOR: Color of the husk at 65 days after silking according to the Munsell color chart.

HKCF=HUSK FRESH COLOR: Color of the husk at 25 days after silking according to the Munsell color chart.

HKL=EAR HUSK LENGTH: The measure at harvest of the husk length on a 1 to 4 scale where 1 is short (ear exposed), 2 is medium (<8 cm), 3 is long (8-10 cm) and 4 is very long (>10 cm). Measurements in cm are how far the husk extends past the end of the ear; length between the ear tip and end of the husk.

HKT=HUSK TIGHTNESS: The relative measure of husk tightness at 65 days after silking on a 1 to 9 scale where 1 is very loose and 9 is very tight HYBRID VARIETY: A substantially heterozygous hybrid line and minor genetic variants thereof that retain the overall genetics of the hybrid line including but not limited to a locus conversion, a mutation, a somoclonal variant, or a gene-edited variant.

INBRED: A variety developed through inbreeding or doubled haploidy that preferably comprises homozygous alleles at about 95% or more of its loci. An inbred can be reproduced by selfing or growing in an isolation so that the plants can only pollinate with the same inbred variety.

INTROGRESSION: A breeding process or tool for transferring genetic material from one genotype to another.

ITL=INTERNODE LENGTH: The length measured in cm of the internode located between the ear leaf node and the next highest node. The ear leaf node is the nodal point of attachment of the highest significant ear.

KNCPC=KERNEL CAP COLOR: Rated at harvest in the middle of the uppermost ear on a 1 to 5 scale where 1 is white, 2 is light yellow, 3 is yellow, 4 is orange, and 5 is other.

KNL=KERNEL LENGTH (DEPTH): The measure in mm of the length from the kernel cap to the tip.

KNSC=KERNEL SIDE COLOR: Rated at harvest in the middle of the uppermost ear on a 1 to 5 scale where 1 is white, 2 is light yellow, 3 is yellow, 4 is orange, and 5 is other.

KNT=KERNEL THICKNESS: The measure in mm of the mid-point thickness of the kernel on the narrow side.

KNW=KERNEL WIDTH: The measure in mm of the mid-point width of the kernel on the front (embryo) or back (distal) sides.

KNWT=ONE HUNDRED KERNEL WEIGHT: The weight in grams of 100 random and unsized kernels from the ear.

LFAEN=LEAF NUMBER ABOVE THE EAR: The number of leaves above the ear leaf node (not including the ear leaf).

LFAGL=LEAF ANGLE BETWEEN BLADE AND STEM: A measure of the adaxial angle formed between stem and leaf blade. Reported on the leaf located two leaves above the ear leaf node.

LFC=LEAF COLOR: A measure of the green coloration intensity in the leaves, rated on a 1 to 4 scale where 1 is light green, 2 is medium green, and 3 is dark green, and 4 is very dark green. Reported on the leaf located two leaves above the ear leaf node.

LFLC=LEAF LONGITUDAL CREASES: A relative measure of the longitudinal creases of the ear leaf on a 1 to 9 scale where 1 is none and 9 is many.

LFMW=LEAF MARGINAL WAVES: A relative measure of the leaf marginal waves of the ear leaf on a 1 to 9 scale where 1 is none and 9 is many.

LINKAGE: Refers to a phenomenon wherein alleles on the same chromosome tend to segregate together more often than expected by chance if their transmission was independent.

LOCUS: A specific location on a chromosome.

LOCUS CONVERSION or TRAIT CONVERSION: A locus conversion refers to plants within a variety that have been modified in a manner that retains the overall genetics of the variety and further comprises one or more loci with a specific desired trait. Such as male sterility, insect control, disease control or herbicide tolerance. Examples of single locus conversions include mutant genes, transgenes, gene-edited alleles/genes, and native traits finely mapped to a single locus. One or more locus conversion traits may be introduced into a single corn variety.

MAIZE DWARF MOSAIC COMPLEX (MDMV=Maize Dwarf Mosaic Virus and MCDV=Maize Chlorotic Dwarf Virus): A 1 to 9 visual rating indicating the resistance to Maize Dwarf Mosaic Complex. A higher score indicates a higher resistance. Data are collected only when sufficient selection pressure exists in the experiment measured.

MALE STERILITY: A male sterile plant is one which produces no pollen or no viable pollen (pollen that is able to fertilize the egg to produce a viable seed) by means of the plant genetics, biotechnology manipulation, or mechanical manipulation.

MST=HARVEST MOISTURE: The percentage moisture of the grain at harvest.

NEI DISTANCE: A quantitative measure of percent similarity between two varieties. Nei's distance between varieties A and B can be defined as 1-(2*number alleles in common/(number alleles in A+number alleles in B). For example, if varieties A and B are the same for 95 out of 100 alleles, the Nei distance would be 0.05. If varieties A and B are the same for 98 out of 100 alleles, the Nei distance would be 0.02. Free software for calculating Nei distance is available on the internet at multiple locations such as, for example, at: evolution-genetics.washington.edu/phylip.html. See Nei, Proc Natl Acad Sci, 76:5269-5273 (1979) which is incorporated by reference for this purpose.

NORTHERN LEAF BLIGHT (*Helminthosporium turcicum* or *Exserohilum turcicum*): A 1 to 9 visual rating indicating the resistance to Northern Leaf Blight. A higher score indicates a higher resistance. Data are collected only when Sufficient selection pressure exists in the experiment measured.

PERCENT IDENTITY: Percent identity as used herein refers to the comparison of the alleles present in two varieties. For example, when comparing two inbred plants to each other, each inbred plant will have the same allele (and therefore be homozygous) at almost all of their loci. Percent identity is determined by comparing a statistically significant number of the homozygous alleles of two varieties. For example, a percent identity of 90% between SG350 and another variety means that the two varieties have the same homozygous alleles at 90% of their loci. This is usually measured by comparing the genotypic SNP profile or other molecular marker profile between the two varieties.

PHT=PLANT HEIGHT: This is a measure in cm of the height of the plant from the ground to the tip of the tassel.

PLANT: As used herein, the term "plant" includes reference to an immature or mature whole plant, including a plant that has been detasseled or from which seed or grain has been removed. The seed or embryo that will produce the plant is also considered to be the plant.

PLANT PART: As used herein, the term "plant part" includes leaves, stems, roots, seed, grain, embryo, pollen, ovules, flowers, ears, cobs, husks, stalks, root tips, anthers, pericarp, silk, tissue, cells and the like.

PLANT POPULATION: A measure of the number of seeds planted in a field or test plot, or the number of plants emerged in a field. Recorded as 1000s per acre.

PLATFORM: Refers to a variety of certain base genetics and this variety with the base genetics comprising a locus conversion or other variant. There can be a platform for the inbred maize variety and the hybrid maize variety.

POL=POLLEN SCORE: A relative measure of the amount of pollen being shed by a tassel rated on a 0 to 9 scale where 0 (zero) is male sterile and 9 is heavy pollen shed. The higher the score the more pollen shed.

PREDICTED RELATIVE MATURITY: This trait is based on the harvest moisture of the grain. The relative maturity rating is based on a known set of checks and utilizes standard linear regression analyses and is also referred to as the Comparative Relative Maturity Rating System that is similar to the Minnesota Relative Maturity Rating System.

RESISTANCE: Synonymous with tolerance. The ability of a plant to withstand exposure to an insect, disease, herbicide or other biotic or abiotic stress. A resistant plant variety will have a level of resistance higher than a comparable susceptible variety.

RTLPE=EARLY ROOT LODGING PERCENTAGE: The percentage of plants that root lodge prior to or around anthesis; plants that lean from the vertical axis at an approximately 30-degree angle or greater would be counted as root lodged. Data are collected only when sufficient selection pressure exists in the experiment measured.

RTLPF=LATE ROOT LODGING PERCENTAGE: The percentage of plants that root lodge after anthesis through harvest; plants that lean from the vertical axis at an approximately 30-degree angle or greater would be counted as root lodged. Data are collected only when sufficient selection pressure exists in the experiment measured.

SDV=SEEDLING VIGOR RATING: This is a measure of the relative height and size of a corn seedling at the V4 stage of growth on a 1 to 9 scale where 1 is weak or slow growth, 5 is average growth, and 9 is strong growth. Taller plants, wider leaves, more green mass and darker color constitute higher scores.

SEED: Fertilized and ripened ovule, consisting of the plant embryo, varying amounts of stored food material, and a protective outer seed coat. Synonymous with grain.

SELF POLLINATION: A plant is self-pollinated if pollen from one flower is transferred to the same or another flower of the same plant. Pollen from the tassel of a corn plant is applied to the ear silk of the same corn plant.

SGR=STAY GREEN: Stay green is the measure of plant health measured at 65 days after Bilking or close to black layer formation (physiological maturity). Reported on a 1 to 9 scale where 1 is worst with early dieback and 9 is best with late dieback. Higher score indicate better late-season plant health.

SHDD=NUMBER OF DAYS FROM EMERGENCE TO SHED.

SHDGDU=GDU TO SHED: The number of growing degree units (GDUs) or heat units required for an inbred variety or hybrid to develop from emergence to 50 percent of the plants shedding pollen. Growing degree units are calculated by the Barger Method as given in the GDU definition.

SHKL=EAR SHANK LENGTH: A measure in cm of the length of the ear shank from the ear base to the attachment point to the stalk.

SHP=LEAF SHEATH PUBESCENCE SCALE: The relative measure of leaf sheath pubescence on a 1 to 9 scale where 1 is none and 9 is like peach fuzz. Reported on the leaf sheath located two leaves above the ear leaf node.

SIB POLLINATION: A plant is sib-pollinated when individuals within the same family or variety are used for pollination.

SITE SPECIFIC INTEGRATION: Genes that create a site for site specific DNA integration. This includes the introduction of FRT sites that may be used in the FLP/FRT system and/or Lox sites that may be used in the Cre/Loxp system. For example, see Lyznik, et al., Site-Specific Recombination for Genetic Engineering in Plants, Plant Cell Rep (2003) 21:925-932 and WO99/25821.

SKC=SILK COLOR: A measure of the silk color at silk emergence and after the silks have been exposed to the sun briefly to allow color development (3-days after R1). Reported on a 1 to 9 scale where 1 is green, 2 is yellow, 3 is pink, 5 is red, 7 is dark red, and 9 is purple.

SLKD=NUMBER OF DAYS FROM EMERGENCE TO SILK.

SLKGDU=GDU TO SILK: The number of growing degree units required for an inbred or hybrid to develop from emergence to 50 percent of the plants at silk emergence (R1). Growing degree units are calculated by the Barger Method as given in the GDU definition.

SNP=SINGLE NUCLEOTIDE POLYMORPHISM: A DNA sequence variation occurring when a single nucleotide in the genome differs between individual plants or plant varieties. The differences can be equated to different alleles and indicate identifiable and measurable polymorphisms between alleles. These polymorphisms are used as a genetic marker system (SNPs) for plant and animal study. A number of SNP markers can be used to determine a genotype or molecular profile of an individual plant or plant variety and can be used to compare similarities and differences among plants and plant varieties.

SOUTHERN LEAF BLIGHT (*Helminthosporium maydis* or *Bipolaris maydis*): A 1 to 9 visual rating indicating the resistance to Southern Leaf Blight. A higher score indicates a higher resistance. Data are collected only when sufficient selection pressure exists in the experiment measured.

SOUTHERN RUST (*Puccinia polysora*): A 1 to 9 visual rating indicating the resistance to Southern Rust. A higher score indicates a higher resistance. Data are collected only when sufficient selection pressure exists in the experiment measured.

Stewart's Wilt (*Erwinia stewartii*): A 1 to 9 visual rating indicating the resistance to Stewart's Wilt. A higher score indicates a higher resistance. Data are collected only when sufficient selection pressure exists in the experiment measured.

SSRs=Single Sequence Repeats: Genetic markers based on polymorphisms in repeated nucleotide sequences, such as microsatellites.

STLP=STALK LODGING PERCENTAGE: The percentage of plants that stalk lodged (stalk breakage) at harvest (when grain moisture is between about 20% and 30%) as measured by the percentage of plants that had broken below the ear. Data are collected only when sufficient selection pressure exists in the experiment measured.

TLPSTK=TILLERS PER STALK: An average count of the number of tillers per plant. A tiller is a secondary shoot that usually develops from the basal nodes of the plant. A countable tiller is one that reaches a height of 30 cm or taller.

TSBAGL=TASSEL BRANCH ANGLE: The adaxial angle between the tassel central spike and the primary branches. Reported from the second branch from the bottom of the tassel.

TSBAT=TASSEL BRANCH ATTITUDE: Measured from the main spike to the tassel branch tip on a 1 to 3 scale where 1 is erect, 2 is horizontal, and 3 is drooping.

TSCSL=LENGTH OF TASSEL CENTRAL SPIKE: The length in cm of the tassel central spike from the uppermost lateral branch to the tip.

TSL=TASSEL LENGTH: The measure in cm from the flag leaf collar to the tassel tip.

TSPB=NUMBER OF PRIMARY LATERAL TASSEL BRANCHES: The number of primary lateral tassel branches; not including secondary lateral branches which originate from primary lateral branches.

TSPL=TASSEL PEDUNCLE LENGTH: The measure in cm from the top leaf node (flag leaf node) to the bottom primary lateral tassel branch.

TWT=TEST WEIGHT: The measure of the weight of the grain in pounds for a given volume (bushel).

VARIETY: A maize line or hybrid and minor genetic modifications there of that retain the overall genetics of the line including but not limited to a locus conversion, a mutation, a somoclonal variant, or gene-edited variant.

YLDADJ=GRAIN YIELD (BUSHELS/ACRE): Yield of the grain at harvest by weight or volume (bushels) per unit area (acre) adjusted to 15.5% moisture.

DETAILED DESCRIPTION OF THE INVENTION AND FURTHER EMBODIMENTS

All tables discussed in the Detailed Description of the Invention and Further Embodiments section can found at the end of the section.

Breeding History of SG350

Inbred maize variety SG350 was developed by the following method. A cross was made between inbred line SG117 and inbred line SG103. Inbred SG350 was developed from this cross by producing a doubled haploid population from the F1 plants, selfing and using ear-to-row selection in the D1 plants, selfing and selecting the D2 plants, and then selfing and bulking from subsequent generations while simultaneously testing for desirable hybrid combinations with established inbreds. Maize variety SG350, being substantially homozygous, can be reproduced by planting seeds of the variety, growing the resulting maize plants under self-pollinating or sib-pollinating conditions with adequate isolation, and harvesting the resulting seed using techniques familiar to the seed corn industry.

Phenotypic Characteristics of SG350

Inbred maize variety SG350 may be used as a male or female in the production of the first generation F1 hybrid. Inbred maize variety SG350 has a relative maturity of approximately 114 days. The variety has shown uniformity and stability within the limits of environmental influence for all the traits as described in the Morphological Characteristics Information (Table 1, found at the end of the section). The variety has been self-pollinated a sufficient number of generations with careful attention paid to uniformity of plant type to ensure the homozygosity and phenotypic stability necessary for use in commercial hybrid seed production. The variety has been increased both by hand and in isolated fields with continued observation for uniformity. No variant traits have been observed or are expected in SG350.

Genotypic Characteristics of SG350

In addition to phenotypic observations, a plant can also be identified by its genotype. The genotype of a plant can be characterized through a genetic marker profile or by DNA sequencing. As a result of using the doubled haploid technique for inbred development, SG350 is substantially homozygous. Because this homozygosity could be characterized by marker profiling or sequencing, an F1 hybrid made with SG350 would substantially comprise the marker profile or DNA sequence of SG350. This is because an F1 hybrid is the sum of its inbred parents, e.g., if one inbred parent is homozygous for allele x at a particular locus, and the other inbred parent is homozygous for allele y at that locus, the F1 hybrid will be xy (heterozygous) at that locus. A genetic marker profile can therefore be used to identify hybrids comprising SG350 as a parent, since such hybrids will comprise two sets of alleles, one set of which will be from SG350. The determination of the male set of alleles and the female set of alleles may be made by marker profiling the hybrid and the pericarp of the hybrid seed, which is composed of maternal parent cells. One way to obtain the paternal parent profile is to subtract the pericarp profile or sequence from the hybrid profile or sequence. Subsequent generations of progeny produced by selection and breeding are expected to be of genotype xx (homozygous), yy (homozygous), or xy (heterozygous) for these locus positions. When the F1 plant is used to produce an inbred, the resulting inbred should be either x or y for that allele. Therefore, in accordance with the above, an embodiment of this invention is a SG350 progeny maize plant or plant part that is a first generation (F1) hybrid maize plant comprising two sets of alleles, wherein one set of the alleles is the same as SG350 at substantially all loci. A maize cell wherein one set of the alleles is the same as SG350 at substantially all loci is also an embodiment of the invention. This maize cell may be a part of a hybrid seed, plant or plant part produced by crossing SG350 with another maize plant.

Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARS), Amplified Fragment Length Polymorphisms (AFLPs), Simple Sequence Repeats (SSRs) which are also referred to as Microsatellites, and Single Nucleotide Polymorphisms (SNPs). For example, see Berry, Don et al., "Assessing Probability of Ancestry Using Simple Sequence Repeat Profiles: Applications to Maize Hybrids and Inbreds", Genetics, 2002, 161:813-824, and Berry, Don et al., "Assessing Probability of Ancestry Using Simple Sequence Repeat Profiles: Applications to Maize Inbred Lines and Soybean Varieties", Genetics, 2003, 165: 331-342.

Particular markers used for these purposes are not limited to the set of markers disclosed herein but may include any type of marker and marker profile which provides a means of distinguishing varieties. In addition to being used for identification of maize variety SG350, a hybrid produced through the use of SG350, and the identification or verification of pedigree for progeny plants produced through the use of SG350, a genetic marker profile is also useful in developing a locus conversion of SG350.

Means of performing genetic marker profiles using SNP and SSR polymorphisms are well known in the art. SNPs are genetic markers based on a polymorphism in a single nucleotide. A marker system based on SNPs can be highly informative in linkage analysis relative to other marker systems in that multiple alleles may be present. SG350 and its plant parts can be identified through a molecular marker profile. Such plant parts may be either diploid or haploid. Also encompassed within the scope of the invention are plants and plant parts substantially benefiting from the use of SG350 in their development, such as SG350 comprising a locus conversion or comprising a single gene-edited locus or multiple gene-edited loci.

Comparing SG350 to Other Inbreds

A breeder uses various methods to help determine which plants should be selected from segregating populations and ultimately which inbred varieties will be used to develop hybrids for commercialization. In addition to knowledge of the germplasm and plant genetics, a part of the selection process is dependent on experimental design coupled with the use of statistical analysis. Experimental design and statistical analysis are used to help determine which plants, which family of plants, and finally which inbred varieties and hybrid combinations are significantly better or different for one or more traits of interest. Experimental design methods are used to assess error so that differences between two inbred varieties or two hybrid varieties can be more accurately evaluated. Statistical analysis includes the calculation of mean values, determination of the statistical significance of the sources of variation, and the calculation of the appropriate variance components. Either a five or a one percent significance level is customarily used to determine whether a difference that occurs for a given trait is real or due to the environment or experimental error. One of ordinary skill in the art of plant breeding would know how to evaluate the traits of two plant varieties to determine if there is a significant difference between the two traits expressed by those varieties. For example, see Fehr, Walt, Principles of Cultivar Development, p. 261-286 (1987). Mean trait values may be used to determine whether trait differences are significant. Trait values should preferably be measured on plants grown under the same environmental conditions, and environmental conditions should be appropriate for the traits or traits being evaluated. Sufficient selection pressure should be present for optimum measurement of traits of interest such as herbicide tolerance, insect or disease resistance, or environmental stress tolerance. A locus conversion of SG350 for herbicide tolerance (for example) should be compared with an isogenic counterpart in the absence of the converted trait. In addition, a locus conversion for insect or disease resistance should be compared to the isogenic counterpart, in the absence of disease pressure or insect pressure.

Development of Maize Hybrids Using SG350

A single cross maize hybrid results from the cross of two inbred varieties, each of which has a genotype that complements the genotype of the other. A hybrid progeny of the first generation is designated F1. In the development of commercial hybrids in a maize plant breeding program, only the F1 hybrid plants are sought. F1 hybrids are more vigorous than their inbred parents. This hybrid vigor, or heterosis, can be manifested in many polygenic traits, including increased vegetative growth and increased grain yield.

SG350 may be used to produce hybrid maize. One such embodiment is the method of crossing maize variety SG350 with another maize plant, such as a different maize variety, to form a first generation F1 hybrid seed. The first generation F1 hybrid seed, plant and plant part produced by this method is an embodiment of the invention. The first generation F1 seed, plant and plant part will comprise an essentially complete set of the alleles of variety SG350. One of ordinary skill in the art can utilize molecular methods to identify a particular F1 hybrid plant produced using variety SG350. Further, one of ordinary skill in the art may also produce F1 hybrids with transgenic, male sterile, gene-edited, and/or locus conversions of variety SG350. The development of a maize hybrid in a maize plant breeding program involves three steps: (1) the selection of plants from various germplasm pools for initial breeding crosses; (2a) the selfing of the selected plants from the breeding crosses for several generations to produce a series of varieties, such as SG350, which although different from each other, breed true and are highly uniform; or (2b) subjecting the F1 breeding cross seed to a doubled haploid method to develop a DH population of D1 seed followed by multiple rounds of varietal selection, and selfing to establish one or more varieties from the DH population; and (3) crossing the selected varieties with different varieties to produce the hybrids. During the inbreeding process in maize, the vigor of the varieties decreases, and so one would not be likely to use SG350 directly to produce grain. Similarly, the development of an inbred variety like SG350 through a DH method would also produce a less vigorous plant. However, vigor is restored when SG350 is crossed to a different inbred variety to produce a commercial F1 hybrid. An important consequence of the homozygosity and homogeneity of the inbred variety is that the hybrid between a defined pair of inbreds may be reproduced indefinitely as long as the homogeneity of the inbred parents is maintained.

SG350 may be used to produce a single cross hybrid, a double cross hybrid, or a three-way hybrid. A single cross hybrid is more common and is produced when two inbred varieties are crossed to produce the F1 progeny. A double cross hybrid is produced from four inbred varieties crossed in pairs (A times B and C times D) and then the two F1 hybrids are crossed again (A times B) times (C times D). A three-way cross hybrid is produced from three inbred varieties where two of the inbred varieties are crossed (A times B) and then the resulting F1 hybrid is crossed with the third inbred (A times B) times C. In each case, pericarp tissue from the female parent will be a part of and protect the hybrid seed.

Molecular data such as DNA or RNA sequence from SG350 may be used in a plant breeding process. Nucleic acids may be isolated from a seed of SG350 or from a plant, plant part, or cell produced by growing a seed of SG350, or from a seed of SG350 with a locus conversion or gene edited locus, or from a plant, plant part, or cell of SG350 with a locus conversion or gene edited locus. One or more polymorphisms may be identified and isolated from the nucleic acids. In turn these identified DNA polymorphisms could be correlated with a phenotype or trait of interest or a performance advantage. A plant having one or more of the identified polymorphisms may be selected and used in a plant breeding method to produce another plant.

Combining Ability of SG350

Combining ability of a variety, as well as the performance of the variety per se, is a factor in the selection of improved maize inbreds. Combining ability refers to a variety's contribution as a parent when crossed with other varieties to form hybrids. The initial experimental hybrids formed for the purpose of selecting superior varieties may be referred to as test crosses and include comparisons to other hybrid varieties grown in the same environment (same cross, location and time of planting). One way of measuring combining ability is by using values based in part on the overall mean of a number of test crosses weighted by number of experiment and location combinations in which the hybrid combinations occurs. The mean may be adjusted to remove environmental effects and known genetic relationships among the varieties. General combining ability provides an overall score for the inbred over a large number of test crosses. Specific combining ability provides information on hybrid combinations formed by SG350 and a specific inbred parent. A variety such as SG350 which exhibits good general combining ability may be used in a large number of hybrid combinations.

Hybrid Comparisons

These hybrid comparisons in Table 2 represent specific hybrid crosses with SG350 and a comparison of these specific hybrids with other hybrids with favorable characteristics. These comparisons illustrate the good specific combining ability of SG350. The results in Table 2 compare a specific hybrid for which SG350 is a parent with other hybrids. The data in Table 2 shows that several F1 hybrids created with SG350 have been reduced to practice. These comparisons illustrate the good specific combining ability of SG350 The data presented for these hybrids is based on replicated field trials.

Locus Conversions of SG350

SG350 represents a new base genetic variety into which a new locus may be introgressed. Direct transformation and backcrossing represent two important methods that can be used to accomplish such an introgression. The term locus conversion is used to designate the product of such an introgression or trait conversion.

A locus conversion of SG350 will retain the genetic integrity of SG350. A reasonably successful locus conversion of SG350 will comprise at least 90%, 91%, 92%, 93%, 94%, 95%, 96%, 97%, 98% or 99% of the genetic identity of SG350 as determined by using SSR markers or SNP markers. For example, a locus conversion of SG350 can be developed when DNA sequences are introduced through backcrossing (Hallauer et al. in Corn and Corn Improvement, Sprague and Dudley, Third Ed. 1998), with SG350 utilized as the recurrent parent. Both naturally occurring and transgenic DNA sequences may be introduced through backcrossing techniques. A backcross conversion may produce a plant with a trait or locus conversion in at least one or more backcrosses, including at least 2 crosses, at least 3 crosses, at least 4 crosses, at least 5 crosses and the like. Molecular marker assisted breeding or selection, or marker assisted backcrossing may be utilized to reduce the number of backcrosses necessary to achieve the backcross conversion. For example, see Openshaw, S. J. et al., Marker-assisted Selection in Backcross Breeding, In: Proceedings Symposium of the Analysis of Molecular Data, August 1994, Crop Science Society of America, Corvallis, Oreg., where it is demonstrated that a locus conversion can be made in as few as two backcrosses.

The complexity of the backcross conversion method depends on the type of trait being transferred (single genes or closely linked genes versus unlinked genes), the level of expression of the trait, the type of inheritance (cytoplasmic or nuclear) and the types of parents included in the cross. It is understood by those of ordinary skill in the art that for single locus traits that are relatively easy to classify, the backcross method is effective and relatively easy to manage. (See Hallauer et al. in Corn and Corn Improvement, Sprague and Dudley, Third Ed. 1998). Desired traits that may be transferred through locus conversion include, but are not limited to, waxy starch, sterility (nuclear and cytoplasmic), fertility restoration, grain color (white), nutritional enhancements, drought resistance, enhanced nitrogen utilization efficiency, altered nitrogen responsiveness, altered fatty acid profile, increased digestibility, low phytate, industrial enhancements, disease resistance (bacterial, fungal or viral), insect resistance, herbicide tolerance and yield enhancements. A locus conversion, also called a trait conversion, can be a native trait, a trait derived by gene-editing, or a transgenic trait likely obtained from a different species from maize. In addition, an introgression site itself, such as an FRT site, Lox site or other site-specific integration site, may be inserted by backcrossing or gene-editing and utilized for direct insertion of one or more genes of interest into a specific plant variety. The seed industry commonly markets "triple stacks" of base genetics; which can be varieties comprising a locus conversion of at least 3 genes. Similarly, "quadruple stacks" would comprise the base genetics and could comprise a locus conversion of at least 4 genes. A single locus may contain several transgenes, such as a transgene for disease resistance that, in the same expression vector, also contains a transgene for herbicide tolerance. As used herein, the phrase "comprising a transgene, transgenic event, locus conversion, or gene-edited locus" means one or more transgenes, transgenic events, locus conversions, or gene-edited loci. The gene for herbicide tolerance may be used as a selectable marker and/or as a phenotypic trait. A locus conversion of a site-specific integration system allows for the integration of multiple genes at the converted loci. Further, SSI and FRT technologies known to those of skill in the art may result in multiple gene introgressions at a single locus. Similarly, those with knowledge of gene-editing should be able to insert multiple genes in the same locus.

The locus conversion or gene-edited locus may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele, such as the waxy starch characteristic, requires growing and selfing the first backcross generation to determine which plants carry the recessive alleles through expression of the recessive trait in a homozygous state. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype and/or genotype of the recurrent parent. While occasionally additional polynucleotide sequences or genes may be transferred along with the backcross conversion, the backcross conversion variety "fits into the same hybrid combination as the recurrent parent inbred variety and contributes the effect of the additional locus added through the backcross." ((Poehlman et al (1995) Breeding Field Crop, 4th Ed., Iowa State University Press, Ames, Iowa, pp. 132-155 and 321-344)). When one or more traits are introgressed into the variety a difference in quantitative agronomic traits, such as yield or dry down, between the variety and an introgressed version of the variety in some environments may occur. For example, the introgressed version may provide a net yield increase in environments where the trait provides a benefit, such as when a variety with an introgressed trait for insect resistance is grown in an environment where insect pressure exists, or when a variety with herbicide tolerance is grown in an environment where herbicide is used.

The typical backcrossing process for adding or modifying a trait or locus in maize variety SG350 comprises (1) crossing SG350 plants grown from SG350 seed with plants of another maize variety that comprise the desired trait or locus; (2) selecting F1 progeny plants that comprise the desired trait or locus to produce selected F1 progeny plants; (3) crossing the selected progeny plants with the SG350 recurrent parent plants to produce backcross progeny plants; (4) selecting for backcross progeny plants that have the desired trait or locus and the phenotypic characteristics of maize variety SG350 to produce selected backcross progeny plants; and (5) backcrossing to SG350 one or more times in succession as the recurrent parent to produce backcross progeny plants that comprise said trait or locus. The modified SG350 may be further characterized as having essentially the same phenotypic characteristics of maize variety SG350 listed in Table 1 and/or may be characterized by percent identity to SG350 as determined by molecular markers, such as SSR markers or SNP markers or through genomic sequence comparisons.

In addition, the above process and other similar processes described herein may be used to produce F1 hybrid maize seed by adding a step at the end of the process that comprises crossing SG350 with the locus conversion with a different maize plant and harvesting the resultant F1 hybrid maize seed. This "stacking" of traits is typically used in the hybrid seed industry and known to those who practice the art.

Traits are also used by those of ordinary skill in the art to characterize progeny. Traits are commonly evaluated at a significance level, such as a 1%, 5% or 10% significance level, when measured in plants grown in the same environmental conditions.

Male Sterility and Hybrid Seed Production

Hybrid seed production requires elimination or inactivation of pollen produced by the female inbred parent. Incomplete removal or inactivation of the pollen provides the potential for self-pollination. A reliable method of controlling male fertility in plants offers the opportunity for improved seed production.

SG350 can be produced in a male-sterile form. There are several ways in which a maize plant can be manipulated so that it is male sterile. These include use of manual or mechanical emasculation (or detasseling), use of one or more genetic factors that confer male sterility, including cytoplasmic genetic and/or nuclear genetic male sterility, use of gametocides and the like. A male sterile designated SG350 may include one or more genetic factors, which result in cytoplasmic genetic and/or nuclear genetic male sterility. All of such embodiments are within the scope of the present claims. The male sterility may be either partial or complete male sterility.

Hybrid maize seed is often produced by a male sterility system incorporating manual or mechanical detasseling. Alternate strips of two maize inbreds (a male and a female) are planted in a field, and the pollen-bearing tassels are removed from the female inbreds. Provided that there is sufficient isolation from sources of foreign maize pollen, the ears of the detasseled female inbred will be fertilized only from the other inbred (male), and the resulting seed is therefore hybrid and will form hybrid plants.

The laborious detasseling process can be avoided by using cytoplasmic male-sterile (CMS) inbreds. Plants of a CMS inbred are male sterile as a result of genetic factors in the cytoplasm, as opposed to the nucleus, and so nuclear linked genes are not transferred during backcrossing. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile, and either option may be preferred depending on the intended use of the hybrid. The same hybrid seed, a portion produced from detasseled fertile maize and a portion produced using the CMS system, can be blended to ensure that adequate pollen loads are available for fertilization when the hybrid plants are grown. CMS systems have been successfully used since the 1950's, and the male sterility trait is routinely backcrossed into female inbred varieties. See Wych, Robert D. (1988) "Production of Hybrid Seed", Corn and Corn Improvement, Ch. 9, pp. 565-607.

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describes a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed and expressed.

These, and the other methods of conferring genetic male sterility in the art, each possess their own benefits and drawbacks. Some other methods use a variety of approaches such as delivering into the plant a gene encoding a cytotoxic substance associated with a male tissue specific promoter or an antisense system in which a gene critical to fertility is identified and an antisense to that gene is inserted in the plant (see Fabinjanski, et al. EPO 89/3010153.8 publication no. 329,308 and PCT application PCT/CA90/00037 published as WO 90/08828). Another system for controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, Glenn R., and U.S. Pat. No. 4,936,904). Application of the gametocide, timing of the application and genotype specificity often limit the usefulness of the approach and it is not appropriate in all situations. Incomplete control over male fertility may result in self-pollinated seed being unintentionally harvested and packaged with hybrid seed. This would typically be only female parent seed, because the male plant is grown in rows that are typically destroyed prior to seed development. Once the seed from the hybrid bag is planted, it is possible to identify and select these self-pollinated plants. These self-pollinated plants will be one of the inbred varieties used to produce the hybrid. Though the possibility of SG350 being included in a hybrid seed bag exists, the occurrence is very low because much care is taken by seed companies to avoid such inclusions. It is worth noting that hybrid seed is sold to growers for the production of grain or forage and not for breeding or seed production. These self-pollinated plants can be identified and selected by one skilled in the art due to their less vigorous appearance for vegetative and/or reproductive characteristics, including shorter plant height, small ear size, ear and kernel shape, or other characteristics.

Identification of these self-pollinated varieties can also be accomplished through molecular marker analyses or through newer methods such as genotyping by sequencing. See, "The Identification of Female Selfs in Hybrid Maize: A Comparison Using Electrophoresis and Morphology", Smith, J. S. C. and Wych, R. D., Seed Science and Technology 14, 1-8 (1995), the disclosure of which is expressly incorporated herein by reference. Through these technologies, the homozygosity of the self-pollinated variety can be verified by analyzing allelic composition at various loci along the genome. Those methods allow for rapid identification of the invention disclosed herein. See also, "Identification of Atypical Plants in Hybrid Maize Seed by Postcontrol and Electrophoresis" Sarca, V. et al., Probleme de Genetica Teoritica si Aplicata Vol. 20 (1) p. 29-42.

Transformation

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, which are stably inserted into the cell using transformation are referred to herein collectively as "transgenes" and/or "transgenic events". In some embodiments of the invention, a transformed variant of SG350 may comprise at least one transgene but could contain from one to many transgenes inserted into one to many genomic sites. Over the last twenty to twenty-five years several methods for producing transgenic plants have been developed, and the present invention also relates to transformed versions of the claimed maize variety SG350 as well as hybrid combinations thereof.

Numerous methods for plant transformation have been developed, including biological and physical plant transformation protocols. See, for example, Miki et al., "Procedures for Introducing Foreign DNA into Plants" in Methods in Plant Molecular Biology and Biotechnology, Glick, B. R. and Thompson, J. E. Eds. (CRC Press, Inc., Boca Raton, 1993) pages 67-88 and Armstrong, "The First Decade of Maize Transformation: A Review and Future Perspective" (Maydica 44:101-109, 1999), and most recently Lowe et al "Rapid Genotype Independent Zea mays L (Maize) Transformation via Direct Somatic Embryogenesis" (In Vitro Cellular & Developmental Biology-Plant 54:240-252, 2018). In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

A transgenic event which has been stably engineered into the germ cell line of a particular maize plant using transformation techniques, could be moved into the germ cell line of another variety using traditional breeding techniques that are well known in the plant breeding arts. For example, a backcrossing approach is commonly used to move a transgenic event from a transformed maize plant to another variety, and the resulting progeny would then comprise the transgenic event(s). Also, if an inbred variety was used for the transformation then the transgenic plants could be crossed to a different inbred in order to produce a transgenic hybrid maize plant.

Various genetic elements can be introduced into the plant genome using transformation. These elements include but are not limited to genes; coding sequences; inducible, constitutive, and tissue specific promoters; enhancing sequences; and signal and targeting sequences. For example, see the traits, genes and transformation methods listed in U.S. Pat. Nos. 6,118,055 and 6,284,953, which are herein incorporated by reference. In addition, transformability of a variety can be increased by introgressing the trait of high transformability from another variety known to have high transformability, such as Hi-II. See U.S. Patent Application Publication US2004/0016030 (2004). Similarly, transformability can be developed within a maize inbred using recent methods described by Lowe et al In Vitro Cellular and Developmental Biology-Plant 54:240-252, 2018.

With transgenic plants according to the present invention, a foreign protein can be produced in commercial quantities. Thus, techniques for the selection and propagation of transformed plants, which are well understood in the art, yield a plurality of transgenic plants that are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114: 92-6 (1981).

Transgenic events can be mapped by one of ordinary skill in the art and such techniques are well known to those of ordinary skill in the art. For exemplary methodologies in this regard, see for example, Glick and Thompson, Methods in Plant Molecular Biology and Biotechnology 269-284 (CRC Press, Boca Raton, 1993).

Likewise, by means of the present invention, plants can be genetically engineered to express various phenotypes of agronomic interest. Through the transformation of maize, the expression of genes can be altered to enhance disease resistance, insect resistance, herbicide tolerance, agronomic traits, grain quality and other traits. Transformation can also be used to insert DNA sequences which control or help control male-sterility. DNA sequences native to maize as well as non-native DNA sequences can be transformed into maize and used to alter levels of native or non-native proteins. Various promoters, targeting sequences, enhancing sequences, and other DNA sequences can be inserted into the maize genome for the purpose of altering the expression of proteins. Reduction of the activity of specific genes (also known as gene silencing, or gene suppression) is desirable for several aspects of genetic engineering in plants. Many techniques for gene silencing are well known to one of skill in the art, including but not limited to knock-outs (such as by insertion of a transposable element such as mu (Vicki Chandler, The Maize Handbook Ch. 118 (Springer-Verlag 1994) or other genetic elements such as a FRT, Lox or other site specific integration site, antisense technology (see, e.g., Sheehy et al. (1988) PNAS USA 85:8805-8809; and U.S. Pat. Nos. 5,107,065; 5,453,566; and 5,759,829); co-suppression (e.g., Taylor (1997) Plant Cell 9:1245; Jorgensen (1990) Trends Biotech. 8(12):340-344; Flavell (1994) PNAS USA 91:3490-3496; Finnegan et al. (1994) Bio/Technology 12: 883-888; and Neuhuber et al. (1994) Mol. Gen. Genet. 244:230-241); RNA interference (Napoli et al. (1990) Plant Cell 2:279-289; U.S. Pat. No. 5,034,323; Sharp (1999) Genes Dev. 13:139-141; Zamore et al. (2000) Cell 101:25-33; and Montgomery et al. (1998) PNAS USA 95:15502-15507), virus-induced gene silencing (Burton, et al. (2000) Plant Cell 12:691-705; and Baulcombe (1999) Curr. Op. Plant Bio. 2:109-113); target-RNA-specific ribozymes (Haseloff et al. (1988) Nature 334: 585-591); hairpin structures (Smith et al. (2000) Nature 407:319-320; WO 99/53050; and WO 98/53083); MicroRNA (Aukerman & Sakai (2003) Plant Cell 15:2730-2741); ribozymes (Steinecke et al. (1992) EMBO J. 11:1525; and Perriman et al. (1993) Antisense Res. Dev. 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Gene-Editing

Gene-editing or genome editing technologies have been used and commercialized for a number of years with the main component for these technologies being the various nucleases such as zinc-finger nuclease, meganuclease, and/or TALEN, but the potential for this technology has significantly increased recently with the development of the CRISPR-Cas9 nuclease system and related nuclease systems (see reviews by Songstad et al 2017 Critical Reviews in Plant Science, DOI: 10.1080/07352689.2017.1281663, and Ma et al 2017 Molecular Plant 9:961-974, and Townson 2017 BioscienceHorizons volume 10). Use of the rapidly evolving CRISPR systems now allow for those in the art to more easily mutate genes, alter genes by a single nucleotide or multiple nucleotides, remove or replace genes/alleles, suppress or increase expression of alleles, etc. The first published use of CRISPR in maize was by Svitashev et al 2016 (Nature Communications DOI: 10.1038/ncomms13274) where they demonstrated the addition of herbicide resistance and male sterility systems. More recently Shi et al 2017 (Plant Biotechnology Journal 15:207-216) have demonstrated how CRISPR could be used to increase drought resistance of maize by mutating the ARGOS8 gene. While some technical limitations still currently exist, it is clear gene-editing will only increase in importance for agriculture and specifically as a maize breeding tool as this technology advances (Gao 2018 Nature Reviews 19:275-276).

It is possible that plants of the variety SG350 could be modified by gene-editing a trait of interest. Following this initial modification, other traits of interest could be further gene-edited in the variety SG350. Plants, seeds, and cells from such genome edits would be considered derivatives of variety SG350 by their genome remaining substantially variety SG350 genetics, and are hereby claimed. Additionally, other varieties of corn could have allele or locus modifications by gene-editing followed by backcrossing the edited allele or locus into variety SG350 by methods known in the art. Such plants also would substantially be variety SG350 genetics and are also claimed here.

Exemplary nucleotide sequences that may be altered by genetic engineering or gene-editing include, but are not limited to, those categorized below.

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78: 1089 (1994) (*Arabidopsis* RSP2 gene for resistance to *Pseudomonas syringae*), McDowell & Woffenden, (2003) Trends Biotechnol. 21(4): 178-83 and Toyoda et al., (2002) Transgenic Res. 11(6):567-82. A plant resistant to a disease is one that is more resistant to a pathogen as compared to the wild type plant or susceptible plant.

(B) A *Bacillus thuringiensis* protein, a derivative thereof or a synthetic polypeptide modeled thereon. See, for example, Geiser et al., Gene 48: 109 (1986), who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Nos. 40098, 67136, 31995 and 31998. Other non-limiting examples of *Bacillus thuringiensis* transgenes being genetically engineered are given in the following patents and patent applications and hereby are incorporated by reference for this purpose: U.S. Pat. Nos. 5,188,960; 5,689,052; 5,880, 275; 5,986,177; 7,105,332; 7,208,474; WO 91/14778; WO 99/31248; WO 01/12731; WO 99/24581; WO 97/40162 and U.S. application Ser. Nos. 10/032,717; 10/414,637; 11/018, 615; 11/404,297; 11/404,638; 11/471,878; 11/780,501; 11/780,511; 11/780,503; 11/953,648; 11/953,648; and Ser. No. 11/957,893.

(C) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(D) An insect-specific peptide which, upon expression, disrupts the physiology of the affected pest. For example, see the disclosures of Regan, J. Biol. Chem. 269: 9 (1994) (expression cloning yields DNA coding for insect diuretic hormone receptor); Pratt et al., Biochem. Biophys. Res.

Comm. 163: 1243 (1989) (an allostatin is identified in *Diploptera puntata*); Chattopadhyay et al. (2004) Critical Reviews in Microbiology 30 (1): 33-54 2004; Zjawiony (2004) J Nat Prod 67 (2): 300-310; Carlini & Grossi-de-Sa (2002) Toxicon, 40 (11): 1515-1539; Ussuf et al. (2001) Curr Sci. 80 (7): 847-853; and Vasconcelos & Oliveira (2004) Toxicon 44 (4): 385-403. See also U.S. Pat. No. 5,266,317 to Tomalski et al., who disclose genes encoding insect-specific toxins.

(E) An enzyme responsible for a hyperaccumulation of a monterpene, a sesquiterpene, a steroid, hydroxamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23: 691 (1993), who teach the nucleotide sequence of a cDNA encoding tobacco hookworm chitinase, and Kawalleck et al., Plant Molec. Biol. 21: 673 (1993), who provide the nucleotide sequence of the parsley ubi4-2 polyubiquitin gene, and U.S. Pat. Nos. 6,563,020; 7,145,060 and 7,087,810.

(G) A molecule that stimulates signal transduction. For example, see the disclosure by Botella et al., Plant Molec. Biol. 24: 757 (1994), of nucleotide sequences for mung bean calmodulin cDNA clones, and Griess et al., Plant Physiol. 104: 1467 (1994), who provide the nucleotide sequence of a maize calmodulin cDNA clone.

(H) A hydrophobic moment peptide. See PCT application WO 95/16776 and U.S. Pat. No. 5,580,852 disclosure of peptide derivatives of Tachyplesin which inhibit fungal plant pathogens) and PCT application WO 95/18855 and U.S. Pat. No. 5,607,914 (teaches synthetic antimicrobial peptides that confer disease resistance).

(I) A membrane permease, a channel former or a channel blocker. For example, see the disclosure by Jaynes et al., Plant Sci. 89: 43 (1993), of heterologous expression of a cecropin-beta lytic peptide analog to render transgenic tobacco plants resistant to *Pseudomonas solanacearum*.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A virus-specific antibody. See, for example, Tavladoraki et al., Nature 366: 469 (1993), which shows that transgenic plants expressing recombinant antibody genes are protected from virus attack.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., Bio/Technology 10: 1436 (1992). The cloning and characterization of a gene which encodes a bean endopolygalacturonase-inhibiting protein is described by Toubart et al., Plant J. 2: 367 (1992).

(N) A developmental-arrestive protein produced in nature by a plant. For example, Logemann et al., Bio/Technology 10: 305 (1992), have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, S., Current Biology, 5(2) (1995), Pieterse & Van Loon (2004) Curr. Opin. Plant Bio. 7(4):456-64 and Somssich (2003) Cell 113(7):815-6.

(P) Antifungal genes (Cornelissen and Melchers, Pl. Physiol. 101:709-712, (1993) and Parijs et al., Planta 183:258-264, (1991) and Bushnell et al., Can. J. of Plant Path. 20(2):137-149 (1998). Also see U.S. application Ser. Nos. 09/950,933; 11/619,645; 11/657,710; 11/748,994; 11/774,121 and U.S. Pat. Nos. 6,891,085 and 7,306,946.

(Q) Detoxification genes, such as for fumonisin, beauvericin, moniliformin and zearalenone and their structurally related derivatives. For example, see U.S. Pat. Nos. 5,716,820; 5,792,931; 5,798,255; 5,846,812; 6,083,736; 6,538,177; 6,388,171 and 6,812,380.

(R) Cystatin and cysteine proteinase inhibitors. See U.S. Pat. No. 7,205,453.

(S) Defensin genes. See WO03000863 and U.S. Pat. Nos. 6,911,577; 6,855,865; 6,777,592 and 7,238,781.

(T) Genes conferring resistance to nematodes. See e.g. PCT Application WO96/30517; PCT Application WO93/19181, WO 03/033651 and Urwin et al., Planta 204:472-479 (1998), Williamson (1999) Curr Opin Plant Bio. 2(4):327-31; and U.S. Pat. Nos. 6,284,948 and 7,301,069.

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al, *Phytophthora* Root Rot Resistance Gene Mapping in Soybean, Plant Genome IV Conference, San Diego, Calif. (1995).

(V) Genes that confer resistance to Brown Stem Rot, such as described in U.S. Pat. No. 5,689,035 and incorporated by reference for this purpose.

(W) Genes that confer resistance to *Colletotrichum*, such as described in US Patent publication US20090035765 and incorporated by reference for this purpose. This includes the Rcg locus that may be utilized as a single locus conversion.

(X) Genes that confer insect resistance through expression of insecticidal RNAi molecules such as described by Gu et al 2013 Crop Protection 45:36 or claimed in U.S. Pat. No. 8,581,039 or 8,906,876.

2. Transgenes that Confer Tolerance to an Herbicide, for Example:

(A) An herbicide that inhibits the growing point or meristem, such as an imidazolinone or a sulfonylurea. Exemplary genes in this category code for mutant ALS and AHAS enzyme as described, for example, by Lee et al., EMBO J.

7: 1241 (1988), and Miki et al., Theor. Appl. Genet. 80: 449 (1990), respectively. See also, U.S. Pat. Nos. 5,605,011; 5,013,659; 5,141,870; 5,767,361; 5,731,180; 5,304,732; 4,761,373; 5,331,107; 5,928,937; and 5,378,824; U.S. application Ser. No. 11/683,737, and international publication WO 96/33270.

(B) Glyphosate (tolerance imparted by mutant 5-enolpyruvl-3-phosphikimate synthase (EPSPS) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah et al., which discloses the nucleotide sequence of a form of EPSPS which can confer glyphosate tolerance. U.S. Pat. No. 5,627,061 to Barry et al. also describes genes encoding EPSPS enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and U.S. Pat. No. 5,491,288; and international publications EP1173580; WO 01/66704; EP1173581 and EP1173582, which are incorporated herein by reference for this purpose. Glyphosate tolerance is also imparted to plants that express a gene that encodes a glyphosate oxido-reductase enzyme as described more fully in U.S. Pat. Nos. 5,776,760 and 5,463,175, which are incorporated herein by reference for this purpose. In addition, glyphosate tolerance can be imparted to plants by the over expression of genes encoding glyphosate N-acetyltransferase. See, for example, U.S. application Ser. Nos. 10/427,692; 10/835,615 and 11/507,751. A DNA molecule encoding a mutant aroA gene can be obtained under ATCC accession No. 39256, and the nucleotide sequence of the mutant gene is disclosed in U.S. Pat. No. 4,769,061 to Comai. European Patent Application No. 0 333 033 to Kumada et al. and U.S. Pat. No. 4,975,374 to Goodman et al. disclose nucleotide sequences of glutamine synthetase genes which confer tolerance to herbicides such as L-phosphinothricin. The nucleotide sequence of a phosphinothricin-acetyltransferase gene is provided in European Patent No. 0 242 246 and 0 242 236 to Leemans et al. De Greef et al., Bio/Technology 7: 61 (1989), describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1; and U.S. Pat. No. 5,879,903, which are incorporated herein by reference for this purpose. Exemplary genes conferring resistance to phenoxy proprionic acids and cyclohexones, such as sethoxydim and haloxyfop, are the Acc1-51, Acc1-52 and Acc1-53 genes described by Marshall et al., Theor. Appl. Genet. 83: 435 (1992).

(C) An herbicide that inhibits photosynthesis, such as a triazine (psbA and gs+ genes) and a benzonitrile (nitrilase gene). Przibilla et al., Plant Cell 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., Biochem. J. 285: 173 (1992).

(D) Acetohydroxy acid synthase, which has been found to make plants that express this enzyme resistant to multiple types of herbicides, has been introduced into a variety of plants (see, e.g., Hattori et al. (1995) Mol Gen Genet 246:419). Other genes that confer tolerance to herbicides include: a gene encoding a chimeric protein of rat cytochrome P4507A1 and yeast NADPH-cytochrome P450 oxidoreductase (Shiota et al. (1994) Plant Physiol 106:17), genes for glutathione reductase and superoxide dismutase (Aono et al. (1995) Plant Cell Physiol 36:1687, and genes for various phosphotransferases (Datta et al. (1992) Plant Mol Biol 20:619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are tolerant to these herbicides are described in U.S. Pat. Nos. 6,288,306 B1; 6,282,837 B1; and 5,767,373; and international publication WO 01/12825.

3. Transgenes that Confer or Contribute to an Altered Grain Characteristic, Such as:

(A) Altered fatty acids, for example, by (1) Down-regulation of stearoyl-ACP desaturase to increase stearic acid content of the plant. See Knultzon et al., Proc. Natl. Acad. Sci. USA 89: 2624 (1992) and WO99/64579 (Genes for Desaturases to Alter Lipid Profiles in Corn), (2) Elevating oleic acid via FAD-2 gene modification and/or decreasing linolenic acid via FAD-3 gene modification (see U.S. Pat. Nos. 6,063,947; 6,323,392; 6,372,965 and WO 93/11245), (3) Altering conjugated linolenic or linoleic acid content, such as in WO 01/12800, (4) Altering LEC1, AGP, Dek1, Superall, milps, various Ipa genes such as Ipa1, Ipa3, hpt or hggt. For example, see WO 02/42424, WO 98/22604, WO 03/011015, WO02/057439, WO03/011015, U.S. Pat. Nos. 6,423,886, 6,197,561, 6,825,397, and U.S. application Ser. Nos. US2003/0079247, US2003/0204870, and Rivera-Madrid, R. et al. Proc. Natl. Acad. Sci. 92:5620-5624 (1995).

B) Altered phosphorus content, for example, by the (1) Introduction of a phytase-encoding gene would enhance breakdown of phytate, adding more free phosphate to the transformed plant. For example, see Van Hartingsveldt et al., Gene 127: 87 (1993), for a disclosure of the nucleotide sequence of an *Aspergillus niger* phytase gene. (2) Modulating a gene that reduces phytate content. In maize, for example, this could be accomplished, by cloning and then re-introducing DNA associated with one or more of the alleles, such as the LPA alleles, identified in maize mutants characterized by low levels of phytic acid, such as in WO 05/113778 and/or by altering inositol kinase activity as in WO 02/059324, US2003/0009011, WO 03/027243, US2003/0079247, WO 99/05298, U.S. Pat. Nos. 6,197,561, 6,291,224, 6,391,348, WO2002/059324, US2003/0079247, Wo98/45448, WO99/55882, WO01/04147.

(C) Altered carbohydrates affected, for example, by altering a gene for an enzyme that affects the branching pattern of starch or, a gene altering thioredoxin such as NTR and/or TRX (see. (See U.S. Pat. No. 6,531,648 which is incorporated by reference for this purpose) and/or a gamma zein knock out or mutant such as cs27 or TUSC27 or en27 (See U.S. Pat. No. 6,858,778 and US2005/0160488, US2005/0204418; which are incorporated by reference for this purpose). See Shiroza et al., J. Bacteriol. 170: 810 (1988) (nucleotide sequence of *Streptococcus mutans* fructosyl-transferase gene), Steinmetz et al., Mol. Gen. Genet. 200: 220 (1985) (nucleotide sequence of *Bacillus subtilis* levan-sucrase gene), Pen et al., Bio/Technology 10: 292 (1992) (production of transgenic plants that express *Bacillus licheniformis* alpha-amylase), Elliot et al., Plant Molec.

Biol. 21: 515 (1993) (nucleotide sequences of tomato invertase genes), Sogaard et al., J. Biol. Chem. 268: 22480 (1993) (site-directed mutagenesis of barley alpha-amylase gene), and Fisher et al., Plant Physiol. 102: 1045 (1993) (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned herein may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US2004/0034886 and WO 00/68393 involving the manipulation of antioxidant levels, and WO 03/082899 through alteration of a homogentisate geranyl geranyl transferase (hggt).

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US2003/0163838, US2003/0150014, US2004/0068767, U.S. Pat. No. 6,803,498, WO01/79516.

4. Genes that Control Male-Sterility:

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N—Ac-PPT (WO 01/29237).

(B) Introduction of various stamen-specific promoters (WO 92/13956, WO 92/13957).

(C) Introduction of the barnase and the barstar gene (Paul et al. Plant Mol. Biol. 19:611-622, 1992).

For additional examples of nuclear male and female sterility systems and genes, see also, U.S. Pat. Nos. 5,859,341; 6,297,426; 5,478,369; 5,824,524; 5,850,014; and 6,265,640; all of which are hereby incorporated by reference.

5. Genes that create a site for site specific DNA integration. This includes the introduction of FRT sites that may be used in the FLP/FRT system and/or Lox sites that may be used in the Cre/Loxp system. For example, see Lyznik, et al., Site-Specific Recombination for Genetic Engineering in Plants, Plant Cell Rep (2003) 21:925-932 and WO 99/25821 which are hereby incorporated by reference. Other systems that may be used include the Gin recombinase of phage Mu (Maeser et al., 1991; Vicki Chandler, The Maize Handbook Ch. 118 (Springer-Verlag 1994), the Pin recombinase of E. coli (Enomoto et al., 1983), and the R/RS system of the pSR1 plasmid (Araki et al., 1992). 6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009; 5,965,705; 5,929,305; 5,891,859; 6,417,428; 6,664,446; 6,706,866; 6,717,034; 6,801,104; WO2000060089; WO2001026459; WO2001035725; WO2001034726; WO2001035727; WO2001036444; WO2001036597; WO2001036598; WO2002015675; WO2002017430; WO2002077185; WO2002079403; WO2003013227; WO2003013228; WO2003014327; WO2004031349; WO2004076638; WO9809521; and WO9938977 describing genes, including CBF genes and transcription factors effective in mitigating the negative effects of freezing, high salinity, and drought on plants, as well as conferring other positive effects on plant phenotype; US2004/0148654 and WO01/36596 where abscisic acid is altered in plants resulting in improved plant phenotype such as increased yield and/or increased tolerance to abiotic stress; WO2000/006341, WO04/090143, U.S. application Ser. Nos. 10/817,483 and 09/545,334 where cytokinin expression is modified resulting in plants with increased stress tolerance, such as drought tolerance, and/or increased yield. Also see WO202776, WO2003052063, JP2002281975, U.S. Pat. No. 6,084,153, WO0164898, U.S. Pat. Nos. 6,177,275, and 6,107,547 (enhancement of nitrogen utilization and altered nitrogen responsiveness). For ethylene alteration, see US20040128719, US20030166197 and WO200032761. For plant transcription factors or transcriptional regulators of abiotic stress, see e.g. US20040098764 or US20040078852.

Other genes and transcription factors that affect plant growth and agronomic traits such as yield, flowering, plant growth and/or plant structure, can be introduced or introgressed into plants, see e.g. WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/

29123, U.S. Pat. Nos. 6,794,560, 6,307,126 (GAI), WO99/09174 (D8 and Rht), WO2004076638 and WO2004031349 (transcription factors).

Using SG350 to Develop Another Maize Plant

Maize varieties such as SG350 are typically developed for use in the production and commercialization of hybrid maize varieties. However, varieties such as SG350 also provide a source of breeding material that may be used to develop new maize inbred varieties. Plant breeding techniques known in the art and used in a maize plant breeding program include, but are not limited to, recurrent selection, mass selection, bulk selection, backcrossing, pedigree breeding, open pollination breeding, genetic marker enhanced selection, making double haploids, mutational breeding, genomic selection, transformation, and gene-editing. Often combinations of these techniques are used. The development of maize hybrids in a maize plant breeding program requires, in general, the development of homozygous inbred varieties, the crossing of these varieties, and the evaluation of the crosses. There are many analytical methods available to evaluate the result of a cross. The oldest and most traditional method of analysis is the observation of phenotypic traits; in particular grain yield, but genotypic analysis may also be used.

This invention is also directed to methods for producing a maize plant by crossing a first parent maize plant with a second parent maize plant wherein either the first or second parent maize plant is a maize plant of the variety SG350. The other parent may be any other maize plant, such as another inbred variety or a plant that is part of a synthetic or natural population. Any such methods using the maize variety SG350 are part of this invention: selfing, ribbing, backcrossing, mass selection, pedigree breeding, bulk selection, genomic selection, hybrid production, crosses to populations, doubled haploid development, and the like. These methods are well known in the art and some of the more commonly used breeding methods are described below. Descriptions of breeding methods can also be found in one of several reference books (e.g., Allard, Principles of Plant Breeding, 1960; Simmonds, Principles of Crop Improvement, 1979; Fehr, "Breeding Methods for Cultivar Development", Production and Uses, 2.sup.nd ed., Wilcox editor, 1987 the disclosure of which is incorporated herein by reference).

Pedigree Breeding

Pedigree breeding simply refers to a selection protocol utilized during the inbreeding process to develop desirable homozygous inbred lines and whereby crosses and selected progeny are closely tracked at each successive generation. The traditional pedigree breeding method of selfing and selection starts with the crossing of two genotypes, such as SG350 and one other inbred variety having one or more desirable characteristics that is lacking or which complements SG350. If the two original parents do not provide all the desired characteristics, other sources can be included in the breeding population. In the traditional pedigree method, superior plants are selfed and selected in successive filial generations. In the succeeding filial generations, the heterozygous condition gives way to homogeneous varieties as a result of self-pollination and selection. Typically, in the traditional pedigree method of breeding, five or more successive filial generations of selfing and selection is practiced: F1 to F2; F2 to F3; F3 to F4; F4 to F5, etc. After a sufficient amount of inbreeding, successive filial generations will serve to increase seed of the developed inbred. Preferably, the inbred variety comprises homozygous alleles at about 95% or more of its loci. At the end of the process, the finished homozygous or near homozygous inbred variety is then used to make an F1 cross with another corn plant to start the selfing and selection process again. While the traditional pedigree breeding method described above is still used by some corn breeding programs, DH methods have now become a preferred method of pedigree breeding due to the advantages of development of a truly homozygous line in less time in comparison to the traditional pedigree breeding method.

Recurrent Selection and Mass Selection

Recurrent selection is a method used in a plant breeding program to improve a population of plants. SG350 is suitable for use in a recurrent selection program. The method entails individual plants cross pollinating with each other to form progeny. The progeny are grown and the superior progeny selected by any number of selection methods, which include individual plant, half-sib progeny, full-sib progeny, selfed progeny and toperossing. The selected progeny are cross pollinated with each other to form progeny for another population. This population is planted and again superior plants for the desired traits are selected to cross pollinate with each other. Recurrent selection is a cyclical process and therefore can be repeated as many times as desired. The objective of recurrent selection is to improve the traits of a population. The improved population can then be used as a source of breeding material to obtain inbred varieties to be used in hybrids or used as parents for a synthetic cultivar. A synthetic cultivar is the resultant progeny formed by the intercrossing of several selected inbreds.

SG350 is suitable for use in mass selection. Mass selection is a useful technique when used in conjunction with molecular marker enhanced selection. In mass selection, seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self-pollination, directed pollination could be used as part of the breeding program.

Genomic Selection

SG350 is suitable for inclusion in a genomic selection program. Genomic selection refers to a breeding tool or process whereby the components of the genetic gain equation (below)

Genetic Gain=(Selection Intensity×Accuracy×Genetic Variance)/Generational Length are manipulated to increase genetic gain. Use of genetic selection tools comprise the development of a training set of genetics whereby both genotype and phenotype are determined experimentally, followed by development of predictive equations that can be used to predict phenotype of unknown varieties by only having determined their genotype. Varieties with the best predictive breeding values are then further advanced for commercial hybrid production and/or recycled into the breeding population for rapid population improvement. These techniques can be adapted into a traditional selfing and selection or DH breeding program to fit the breeding program budget and/or breeding objectives. The greatest advantage of genomic selection is to increase genetic gain primarily by reducing or shortening the breeding cycle. See: Gorjanc et al. BMC Genomics (2016) 17:30; Heffner et al. Crop Science 49:1 (2009); Jannink et al. Briefings in Functional Genomics 9:166 (2010); Scheben et al. Plant Biotechnology Journal 15:149 (2017); Gaynor et al. Crop Science 57:2372 (2017); Zhang et al. G3 7:2315 (2017). The disclosures of which are incorporated herein by reference.

Mutation Breeding

Mutation breeding is one of many methods that could be used to introduce new traits into SG350. SG350 is suitable for use in a mutation breeding program. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "Principles of Cultivar Development" Fehr, 1993 Macmillan Publishing Company, the disclosure of which is incorporated herein by reference. In addition, mutations created in other varieties may be used to produce a backcross conversion of SG350 that comprises such mutation.

Production of Double Haploids

The production of double haploids can also be used for the development of inbreds in the breeding program. For example, an F1 hybrid for which SG350 is a parent can be used to produce double haploid plants. Double haploids are produced by the doubling of a set of chromosomes (1N) from a heterozygous plant to produce a completely homozygous individual. For example, see Wan et al., "Efficient Production of Doubled Haploid Plants Through Colchicine Treatment of Anther-Derived Maize Callus", Theoretical and Applied Genetics, 77:889-892, 1989 and US2003/0005479. This can be advantageous because the process omits the multiple generations of selfing needed to obtain a homozygous plant from a heterozygous source. Haploid induction systems have been developed for various plants to produce haploid tissues, plants and seeds. The haploid induction system can produce haploid plants from almost any genotype by crossing a selected variety (as female) with an inducer variety. Such inducer varieties for maize include Stock 6 (Coe, 1959, Am. Nat. 93:381-382; Sharkar and Coe, 1966, Genetics 54:453-464) RWS (available online from the Universitat Hohenheim), KEMS (Deimling, Roeber, and Geiger, 1997, Vortr. Pflanzenzuchtg 38:203-224), KMS and ZMS (Chalyk, Bylich & Chebotar, 1994, MNL 68:47; Chalyk & Chebotar, 2000, Plant Breeding 119:363-364), and indeterminate gametophyte (ig) mutation (Kermicle 1969 Science 166:1422-1424). The disclosures of which are incorporated herein by reference.

Methods for obtaining doubled haploid plants are also disclosed in Kobayashi, M. et al., Journ. of Heredity 71(1): 9-14, 1980, Pollacsek, M., Agronomie (Paris) 12(3):247-251, 1992; Cho-Un-Haing et al., Journ. of Plant Biol., 1996, 39(3):185-188; Verdoodt, L., et al., February 1998, 96(2): 294-300; Genetic Manipulation in Plant Breeding, Proceedings International Symposium Organized by EUCARPIA, Sep. 8-13, 1985, Berlin, Germany; Chalyk et al., 1994, Maize Genet Coop. Newsletter 68:47; Chalyk, S. T., 1999, Maize Genet. Coop. Newsletter 73:53-54; Coe, R. H., 1959, Am. Nat. 93:381-382; Deimling, S. et al., 1997, Vortr. Pflanzenzuchtg 38:203-204; Kato, A., 1999, J. Hered. 90:276-280; Lashermes, P. et al., 1988, Theor. Appl. Genet. 76:570-572 and 76:405-410; Tyrnov, V. S. et al., 1984, Dokl. Akad. Nauk. SSSR 276:735-738; Zabirova, E. R. et al., 1996, Kukuruza I Sorgo N4, 17-19; Aman, M. A., 1978, Indian J. Genet Plant Breed 38:452-457; Chalyk S. T., 1994, Euphytica 79:13-18; Chase, S. S., 1952, Agron. J. 44:263-267; Coe, E. H., 1959, Am. Nat. 93:381-382; Coe, E. H., and Sarkar, K. R., 1964 J. Hered. 55:231-233; Greenblatt, I. M. and Bock, M., 1967, J. Hered. 58:9-13; Kato, A., 1990, Maize Genet. Coop. Newsletter 65:109-110; Kato, A., 1997, Sex. Plant Reprod. 10:96-100; Nanda, D. K. and Chase, S. S., 1966, Crop Sci. 6:213-215; Sarkar, K. R. and Coe, E. H., 1966, Genetics 54:453-464; Sarkar, K. R. and Coe, E. H., 1971, Crop Sci. 11:543-544; Sarkar, K. R. and Sachan J. K. S., 1972, Indian J. Agric. Sci. 42:781-786; Kermicle J. L., 1969, Mehta Yeshwant, M. R., Genetics and Molecular Biology, September 2000, 23(3):617-622; Tahir, M. S. et al. Pakistan Journal of Scientific and Industrial Research, August 2000, 43(4):258-261; Knox, R. E. et al. Plant Breeding, August 2000, 119(4):289-298; U.S. Pat. No. 5,639,951 and U.S. patent application Ser. No. 10/121,200, the disclosures of which are incorporated herein by reference.

Thus, an embodiment of this invention is a process for making a homozygous SG350 progeny plant substantially similar to SG350 by producing or obtaining a seed from the cross of SG350 and another maize plant and applying double haploid methods to the F1 seed or F1 plant or to any successive filial generation. Such methods decrease the number of generations required to produce an inbred with similar genetics or characteristics to SG350. See Bernardo, R. and Kahler, A. L., Theor. Appl. Genet. 102:986-992, 2001.

In particular, a process of making seed substantially retaining the molecular marker profile of maize variety SG350 is contemplated, such process comprising obtaining or producing F1 hybrid seed for which maize variety SG350 is a parent, inducing double haploids to create progeny without the occurrence of meiotic segregation, obtaining the molecular marker profile of maize variety SG350, and selecting progeny that retain the molecular marker profile of SG350. Another embodiment of the invention is a maize seed derived from inbred maize variety SG350 produced by crossing a plant or plant part of inbred maize variety SG350 with another plant, wherein representative seed of said inbred maize variety SG350 has been deposited and wherein said maize seed derived from the inbred maize variety SG350 has 85%-99% of the same polymorphisms for molecular markers as the plant or plant part of inbred maize variety SG350. The number of molecular markers used for the molecular marker profiling can be 2000 or more. The type of molecular marker used in the molecular profile can be but is not limited to Single Nucleotide Polymorphisms, SNPs. A maize seed derived from inbred maize variety SG350 produced by crossing a plant or plant part of inbred maize variety SG350 with another plant, wherein representative seed of said inbred maize variety SG350 has been deposited and wherein said maize seed derived from the inbred maize variety SG350 has essentially the same morphological characteristics as maize variety SG350 when grown in the same environmental conditions. As used herein, a plant having essentially the same morphological characteristics as maize variety SG350 has at least 50%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or all of the morphological characteristics listed in Tables 1-3 within about 50%, about 40%, about 30%, about 20%, about 15%, about 10%, about 9%, about 8%, about 7%, about 6%, about 5%, about 4%, about 3%, about 2%, about 1% of the measured value or less and/or including measureable characteristics not listed in Tables 1-3. The same environmental conditions may be, but is not limited to a side-by-side comparison. The characteristics can be those listed in Table 1. The comparison can be made using any number of professionally accepted experimental designs and statistical analysis.

Use of SG350 in Tissue Culture

This invention is also directed to the use of SG350 in tissue culture. As used herein, the term "tissue culture" includes plant protoplasts, plant cell tissue culture, cultured microspores, plant calli, plant clumps, somatic embryos, and the like. As used herein, phrases such as "growing the seed" or "grown from the seed" include embryo rescue, isolation of cells from seed for use in tissue culture, as well as traditional growing methods.

Duncan, Williams, Zehr, and Widholm, Planta (1985) 165:322-332 reflects that 97% of the plants cultured that produced callus were capable of plant regeneration. Subsequent experiments with both inbreds and hybrids produced 91% regenerable callus that produced plants. In a further study in 1988, Songstad, Duncan & Widholm in Plant Cell Reports (1988), 7:262-265 reports several media additions that enhance regenerability of callus of two inbred varieties. Other published reports also indicated that "nontraditional" tissues are capable of producing somatic embryogenesis and plant regeneration. K. P. Rao, et al., Maize Genetics Cooperation Newsletter, 60:64-65 (1986), refers to somatic embryogenesis from glume callus cultures and B. V. Conger, et al., Plant Cell Reports, 6:345-347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success. The recent methods described by Lowe et al 2018 (In Vitro Cellular & Developmental Biology-Plant 54:240-252) and references therein further show regenerability and transformability for any variety of maize can be routine the disclosures of which are incorporated herein by reference.

Tissue culture of maize, including tassel/anther culture, is described in U.S. 2002/0062506A1 and European Patent Application, publication EP0160,390, each of which are incorporated herein by reference for this purpose. Maize tissue culture procedures are also described in Green and Rhodes, "Plant Regeneration in Tissue Culture of Maize," Maize for Biological Research (Plant Molecular Biology Association, Charlottesville, Va. 1982, at 367-372) and in Duncan, et al., "The Production of Callus Capable of Plant Regeneration from Immature Embryos of Numerous *Zea Mays* Genotypes," 165 Planta 322-332 (1985). Thus, another aspect of this invention is to provide cells which upon growth and differentiation produce maize plants having the genotype and/or phenotypic characteristics of variety SG350.

Seed Treatments and Cleaning

Another embodiment of this invention is the method of harvesting the seed of the maize variety SG350 as seed for planting. Embodiments include cleaning the seed, treating the seed, and/or conditioning the seed. Cleaning the seed includes removing foreign debris such as weed seed and removing chaff, plant matter, from the seed. Conditioning the seed can include controlling the temperature and rate of dry down and storing seed in a controlled temperature environment. Seed treatment is the application of a composition to the seed such as a coating or powder. Some examples of compositions are insecticides, fungicides, pesticides, antimicrobials, germination inhibitors, germination promoters, cytokinins, growth stimulants, beneficial microbials, and nutrients.

To protect and to enhance yield production and trait technologies, seed treatment options can provide additional crop plan flexibility and cost-effective control against insects, weeds and diseases, thereby further enhancing the invention described herein. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematicides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council, which is hereby incorporated by reference.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis*), *Bradyrhizobium* spp. (including one or more of *betae, canariense, elkanii, iriomotense, japonicum,* liaonigense, *pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCN B, penflufen, *penicillium*, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, *trichoderma*, trifloxystrobin, triticonazole and/or zinc. PCNB seed coat refers to EPA registration number 00293500419, containing quintozen and terrazole. TCMTB refers to 2-(thiocyanomethylthio)benzothiazole. Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

INDUSTRIAL APPLICABILITY

Another embodiment of this invention is the method of harvesting the grain of the F1 plant of variety SG350 and using the grain in a commodity. Examples of maize grain as a commodity include but are not limited to oils, meals, flour, starches, syrups, proteins, and sugars. Maize grain is used as human food, livestock feed, and as raw material in industry. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, is also used extensively as livestock feed, primarily for beef cattle, dairy cattle, hogs, and poultry.

Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications. Plant parts other than the grain of maize are also used in industry: for example, stalks and husks are made into paper and wallboard and cobs are used for fuel and to make charcoal.

The seed of maize variety SG350, the plant produced from the seed, the hybrid maize plant produced from the crossing of the variety, hybrid seed, and various parts of the hybrid maize plant and transgenic versions of the foregoing, can be utilized for human food, livestock feed, and as a raw material in industry. The same is true for substantial derivatives of SG350.

TABLE 1

Morphological Characteristics Information

| Characteristic | Abrev | Units | SG350 Mean | SG350 Std Dev | SG103 Mean | SG103 Std Dev |
|---|---|---|---|---|---|---|
| Flowering | | | | | | |
| Days to 50% silk | SLK Days | Days | 63.5 | 0.8 | 63.1 | 2.0 |
| Heat units to 50% silk | SLKGDU | GDU | 1451 | 15.6 | 1443 | 47.2 |
| Days to 50% shed | SHD Days | Days | 61.9 | 1.1 | 62.5 | 1.8 |
| Heat units to 50% shed | SHDGDU | GDU | 1418 | 22.7 | 1431 | 42.4 |
| Stalk | | | | | | |
| Plant Height | PHT | cm | 187.8 | 5.6 | 208.1 | 15.6 |
| Ear Height | EHT | cm | 59.1 | 7.2 | 62.1 | 6.2 |
| Brace root color | BRC | 1 to 4 | 2.8 | 0.6 | 3.1 | 0.8 |
| Internode length | ITL | cm | 13.8 | 1.0 | 12.4 | 1.9 |
| Avg # ears per stalk | ERPSTK | No. | 1.7 | 0.5 | 1.4 | 0.5 |
| Avg # tillers per stalk | TLPSTK | No. | 0.0 | 0.0 | 0.2 | 0.5 |
| Leaf | | | | | | |
| Color (EL + 2) | LFC | 1 to 4 | 3.0 | 0.0 | 4.0 | 0.0 |
| Length (EL) | ELL | cm | 80.5 | 2.4 | 76.0 | 4.2 |
| Width (EL) | ELW | cm | 8.9 | 0.3 | 9.7 | 0.4 |
| Sheath pubescence (EL + 2) | SHP | 1 to 9 | 1.0 | 0.0 | 1.0 | 0.0 |
| Marginal waves | LFMW | 1 to 9 | 3.2 | 0.7 | 2.7 | 0.8 |
| Longitudal creases | LFLC | 1 to 9 | 3.0 | 0.0 | 2.3 | 0.8 |
| # leaves above top ear | LFAEN | No. | 5.6 | 0.5 | 6.2 | 0.4 |
| Adaxial angle (EL + 2) | LFAGL | angle | 30.5 | 12.4 | 23.4 | 4.7 |
| Tassel | | | | | | |
| Primary branch # | TSPB | No. | 4.4 | 1.4 | 4.2 | 1.3 |
| Angle spike & prim branch | TSBAGL | angle | 37.0 | 10.1 | 31.5 | 6.6 |
| Branch attitude | TSBAT | 1 to 3 | 1.0 | 0.0 | 1.0 | 0.0 |
| Length (leaf collar to tip) | TSL | cm | 37.7 | 1.7 | 46.4 | 3.2 |
| Peduncle length | TSPL | cm | 22.3 | 2.6 | 30.8 | 2.1 |
| Central spike length | TSCSL | cm | 26.6 | 1.8 | 28.1 | 2.7 |
| Rate amount of pollen | POL | 0 to 9 | 4 | | 5 | |
| Anther color (after sun) | ANC | 1 to 9 | 2 | | 2 | |
| Glume color (after sun) | GMC | 1 to 9 | 1 | | 1 | |
| Glume Ring | GMR | 1 or 2 | 1 | | 1 | |
| Bar Glume or Glume bands | GMB | 1 or 2 | 2 | | 1 | |
| Ear Unhusked | | | | | | |
| Silk color (3 Days After R1) | SKC | 1 to 9 | 2 | | 2 | |
| Fresh husk color (25 DAS) | HKCF | Munsell | 5GY5/4 | | 5GY5/8 | |
| Dry husk color (65 DAS) | HKCD | Munsell | 2.5Y8/2 | | 2.5Y8/2 | |
| Ear position (65 DAS) | ERP | 1 to 3 | 1.2 | 0.4 | 1.4 | 0.6 |

TABLE 1-continued

Morphological Characteristics Information

| | | | SG350 | | SG103 | |
|---|---|---|---|---|---|---|
| Characteristic | Abrev | Units | Mean | Std Dev | Mean | Std Dev |
| Husk tightness (65 DAS) | HKT | 1 to 9 | 6.4 | 1.2 | 5.5 | 2.2 |
| Husk cover at harvest | HKL | 1 to 4 | 4.0 | 0.0 | 1.9 | 0.3 |
| Ear Dry and Husked | | | | | | |
| Length | ERL | cm | 14.7 | 1.2 | 18.9 | 2.4 |
| Diameter | ERD | mm | 39.8 | 2.2 | 46.2 | 1.8 |
| Weight | ERWT | gm | 80.0 | 14.1 | 140.6 | 24.2 |
| # Rows of kernels | ERRN | No. | 15.8 | 0.6 | 15.0 | 1.7 |
| # Kernels per row | ERKR | No. | 21.1 | 2.9 | 27.8 | 2.2 |
| Rows identifiable | ERRI | 1 or 2 | 2.0 | 0.0 | 2.0 | 0.0 |
| Row direction/alignment | ERRD | 1 to 3 | 1.0 | 0.0 | 1.0 | 0.0 |
| Ear taper | ERT | 1 to 3 | 2.0 | 0.0 | 2.0 | 0.0 |
| Cob Parameters | | | | | | |
| Cob diameter | CBD | mm | 27.4 | 1.6 | 31.9 | 1.1 |
| Cob color | CBC | 1 to 4 | 3.0 | 0.0 | 3.0 | 0.0 |
| Kernel (dried) | | | | | | |
| Length (depth) | KNL | mm | 10.1 | 0.4 | 10.2 | 0.5 |
| Width | KNW | mm | 7.4 | 0.3 | 8.3 | 0.4 |
| Thickness | KNT | mm | 5.8 | 0.4 | 4.8 | 0.2 |
| Hard Endosperm color | ENDC | 1 to 3 | 2.0 | 0.0 | 2.0 | 0.0 |
| Endosperm type | ENDT | 1 to 10 | 3.0 | 0.0 | 3.0 | 0.0 |
| 100 kernel weight | KNWT | gm | 24.9 | 1.1 | 25.1 | 3.4 |
| Cap color | KNCPC | 1 to 5 | 3.0 | 0.0 | 3.0 | 0.0 |
| Side color | KNSC | 1 to 5 | 2.0 | 0.0 | 2.0 | 0.0 |

TABLE 2

Hybrid Comparisons

| Entry | YLDADJ | MST | TWT | RL | SL | HA |
|---|---|---|---|---|---|---|
| SG17006G | 219.2 | 18.3 | 69.0 | 8.4 | 6.1 | 5.8 |
| SG17005G | 207.9 | 17.1 | 69.3 | 8.9 | 7.5 | 6.0 |

YLDAJD = Yield as Bu/Ac (adjusted to 15.5% moisture)
MST = Moisture at harvest
TWT = Test weight
SL = Stalk lodging 1-9 score (9 = least lodging)
RL = Root lodging 1-9 score (9 = least lodging)
HA = Harvest Appearance 1-9 score (9 = fully intact; intactness of leaves and upper stalks before harvest)

TABLE 3

Hybrid Morphological Characteristics

| | | | Hybrid SG17006G | |
|---|---|---|---|---|
| Characteristic | Abrev | Units | Mean | Std Dev |
| Flowering | | | | |
| Days to 50% silk | SLK Days | Days | 59.3 | 0.5 |
| Heat units to 50% silk | SLKGDU | GDU | 1359 | 13.6 |
| Days to 50% shed | SHD | Days | 59.1 | 0.6 |
| Heat units to 50% shed | SHDGDU | GDU | 1354 | 18.0 |
| Stalk | | | | |
| Plant Height | PHT | cm | 262.8 | 9.0 |
| Ear Height | EHT | cm | 91.2 | 6.9 |
| Brace root color | BRC | 1 to 4 | 1.0 | 0.0 |
| Internode length | ITL | cm | 16.9 | 1.0 |
| Avg # ears per stalk | ERPSTK | No. | 1.4 | 0.5 |
| Avg # tillers per stalk | TLPSTK | No. | 0.3 | 0.5 |
| Leaf | | | | |
| Color (EL + 2) | LFC | 1 to 4 | 3.0 | 0.0 |
| Length (EL) | ELL | cm | 95.1 | 4.0 |

TABLE 3-continued

Hybrid Morphological Characteristics

| | | | Hybrid SG17006G | |
|---|---|---|---|---|
| Characteristic | Abrev | Units | Mean | Std Dev |
| Width (EL) | ELW | cm | 10.1 | 0.4 |
| Sheath pubescence (EL + 2) | SHP | 1 to 9 | 2.3 | 0.5 |
| Marginal waves | LFMW | 1 to 9 | 3.4 | 0.5 |
| Longitudal creases | LFLC | 1 to 9 | 2.0 | 0.0 |
| # leaves above top ear | LFAEN | No. | 6.7 | 0.6 |
| Adaxial angle (EL + 2) | LFAGL | angle | 20.9 | 3.7 |
| Tassel | | | | |
| Primary branch # | TSPB | No. | 7.1 | 1.2 |
| Angle spike & prim branch | TSBAGL | angle | 49.4 | 12.9 |
| Branch attitude | TSBAT | 1 to 3 | 1.0 | 0.0 |
| Length (leaf collar to tip) | TSL | cm | 48.7 | 3.2 |
| Peduncle length | TSPL | cm | 26.1 | 3.1 |
| Central spike length | TSCSL | cm | 29.1 | 2.0 |
| Rate amount of pollen | POL | 0 to 9 | 7 | |
| Anther color (after sun) | ANC | 1 to 9 | 2 | |
| Glume color (after sun) | GMC | 1 to 9 | 1 | |
| Glume Ring | GMR | 1 or 2 | 1 | |
| Bar Glume or Glume bands | GMB | 1 or 2 | 2 | |
| Ear Unhusked | | | | |
| Silk color (3 Days After R1) | SKC | 1 to 9 | 2 | |
| Fresh husk color (25 DAS) | HKCF | Munsell | 5GY6/6 | |
| Dry husk color (65 DAS) | HKCD | Munsell | 2.5Y8/2 | |
| Ear position (65 DAS) | ERP | 1 to 3 | 1.5 | 0.8 |
| Husk tightness (65 DAS) | HKT | 1 to 9 | 5.5 | 0.8 |
| Husk cover at harvest | HKL | 1 to 4 | 2.6 | 0.5 |
| Ear Dry and Husked | | | | |
| Length | ERL | cm | 17.6 | 1.3 |
| Diameter | ERD | mm | 49.7 | 2.1 |
| Weight | ERWT | gm | 182.0 | 55.7 |
| # Rows of kernels | ERRN | No. | 17.1 | 1.2 |
| # Kernels per row | ERKR | No. | 33.8 | 2.6 |
| Rows identifiable | ERRI | 1 or 2 | 2.0 | 0.0 |

TABLE 3-continued

Hybrid Morphological Characteristics

| | | | Hybrid SG17006G | |
|---|---|---|---|---|
| Characteristic | Abrev | Units | Mean | Std Dev |
| Row direction/alignment | ERRD | 1 to 3 | 1.0 | 0.0 |
| Ear taper | ERT | 1 to 3 | 2.0 | 0.0 |
| Cob Parameters | | | | |
| Cob diameter | CBD | mm | 27.0 | 1.3 |
| Cob color | CBC | 1 to 4 | 3.0 | 0.0 |
| Kernel (dried) | | | | |
| Length (depth) | KNL | mm | 13.1 | 0.5 |
| Width | KNW | mm | 8.0 | 0.4 |
| Thickness | KNT | mm | 4.3 | 0.2 |
| Hard Endosperm color | ENDC | 1 to 3 | 2.0 | 0.0 |
| Endosperm type | ENDT | 1 to 10 | 3.0 | 0.0 |
| 100 kernel weight | KNWT | gm | 31.7 | 3.4 |
| Cap color | KNCPC | 1 to 5 | 3.0 | 0.0 |
| Side color | KNSC | 1 to 5 | 2.0 | 0.0 |

Deposits

Applicant has made a deposit of at least 625 seeds of Maize Variety SG350 with the American Type Culture Collection (ATCC), 10801 University Boulevard, Manassas, Va. 20110-2209, USA, with ATCC Deposit No. PTA-125791. The seeds deposited with the ATCC on Mar. 5, 2019 were obtained from the seed of the variety maintained by AgriHorizon, Inc. DBA Seitec Genetics 120 E. Deborah Avenue, Fremont, Nebr. 68002 since prior to the filing date of this application. Access to this seed will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. § 1.808. This deposit of the Maize Variety SG350 will be maintained in the ATCC depository, which is a public depository, for a period of 30 years, or 5 years after the most recent request, or for the enforceable life of the patent, whichever is longer, and will be replaced if it becomes nonviable during that period. Additionally, applicant has or will satisfy all of the requirements of 37 C.F.R. §§ 1.801-1.809, including providing an indication of the viability of the sample upon deposit. Applicant has no authority to waive any restrictions imposed by law on the transfer of biological material or its transportation in commerce. Applicant does not waive any infringement of rights granted under this patent or under the Plant Variety Protection Act (7 USC 2321 et seq.).

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications and alterations may be applied to the compositions and/or methods described herein without departing from the true spirit, concept and scope of the invention.

What is claimed is:

1. A seed, plant, plant part, or plant cell of inbred maize variety SG350, representative seed of the variety having been deposited under ATCC accession number PTA-125791.

2. The plant part of claim 1, wherein the plant part is an ovule or pollen.

3. A maize seed produced by crossing the plant or plant part of claim 1 with a different maize plant.

4. A maize plant produced by growing the maize seed of claim 3.

5. A method for producing a second maize plant, the method comprising applying plant breeding techniques or breeding tools to the plant or plant part of claim 4 to produce the second maize plant.

6. A method for producing a second maize plant or plant part, the method comprising doubled haploid seed generated from a cross of the plant or plant part of claim 4 with an inducer variety, thereby producing the second maize plant or plant part.

7. A method of making a commodity plant product comprising silage, starch, fat, syrup or protein, the method comprising processing the maize plant or plant part of claim 4, thereby producing the commodity plant product.

8. A method of producing a maize plant derived from the variety SG350 comprising: a) crossing the plant of claim 1 with itself or a second plant to produce progeny seed; b) growing the progeny seed to produce a progeny plant and crossing the progeny plant with itself or a different plant to produce further progeny seed; and c) repeating step (b) for at least one additional generation to produce a maize plant derived from the variety SG350.

9. The derived maize plant produced by the method of claim 8, wherein the derived maize plant has the same morphological and physiological characteristics as inbred maize variety SG350 when grown under the same environmental conditions.

10. A method comprising generating a molecular marker profile from nucleic acids isolated from the seed, plant, plant part, or plant cell of claim 1.

11. A converted seed, plant, plant part or plant cell of inbred maize variety SG350, representative seed of the maize variety SG350 having been deposited under ATCC accession number PTA-125791, wherein the converted seed, plant, plant part or plant cell comprises a locus conversion or edited genome, and wherein the plant or a plant grown from the converted seed, plant part or plant cell comprises the locus conversion or edited genome and otherwise has the same morphological and physiological characteristics of maize variety SG350 when grown under the same environmental conditions.

12. The converted seed, plant, plant part or plant cell of claim 11, wherein the locus conversion or edited genome confers a property selected from the group consisting of male sterility, site-specific recombination, abiotic stress tolerance, altered phosphorus, altered antioxidants, altered fatty acids, altered essential amino acids, altered carbohydrates, herbicide tolerance, insect resistance, disease resistance, or enhanced performance.

13. A maize seed produced by crossing the plant or plant part of claim 11 with a different maize plant.

14. A maize plant or plant part produced by growing the seed of claim 13.

15. A method for producing a second maize plant, the method comprising applying plant breeding techniques or breeding tools to the plant or plant part of claim 14 to produce the second maize plant.

16. A method for producing a second maize plant or plant part, the method comprising doubled haploid seed generated from a cross of the plant or plant part of claim 14 with an inducer variety, thereby producing the second maize plant or plant part.

17. A method of making a commodity plant product comprising silage, starch, fat, syrup or protein, the method comprising processing the maize plant or plant part of claim 14, thereby producing the commodity plant product.

18. A method of producing a maize plant derived from the variety SG350, comprising: a) crossing the plant of claim 11 with itself or a second plant to produce progeny seed; b) growing the progeny seed to produce a progeny plant and crossing the progeny plant with itself or a different plant to produce further progeny seed; and c) repeating step (b) for at least one additional generation to produce a maize plant derived from the variety SG350.

19. The derived maize plant produced by the method of claim 18, wherein the derived maize plant has the same morphological and physiological characteristics as inbred maize variety SG350 when grown under the same environmental conditions.

20. A method comprising generating a molecular marker profile from nucleic acids isolated from the seed, plant, plant part, or plant cell of claim 11.

* * * * *